(12) United States Patent
Gitschel et al.

(10) Patent No.: US 8,632,024 B2
(45) Date of Patent: Jan. 21, 2014

(54) SYSTEMS AND METHODS FOR PROCESSING MIXED SOLID WASTE

(75) Inventors: George Gitschel, Redwood, CA (US); Larry T. Buckle, Sacramento, CA (US)

(73) Assignee: Organic Energy Corporation, Sugar Land, TX (US)

( * ) Notice: Subject to any disclaimer, the term of this patent is extended or adjusted under 35 U.S.C. 154(b) by 0 days.

(21) Appl. No.: 13/352,119

(22) Filed: Jan. 17, 2012

(65) Prior Publication Data

US 2012/0190102 A1 Jul. 26, 2012

Related U.S. Application Data

(63) Continuation-in-part of application No. 13/013,707, filed on Jan. 25, 2011, and a continuation-in-part of application No. 13/221,637, filed on Aug. 30, 2011, now Pat. No. 8,398,006, and a continuation of application No. PCT/US2011/068245, filed on Dec. 30, 2011.

(60) Provisional application No. 61/298,208, filed on Jan. 25, 2010.

(51) Int. Cl.
*B02C 19/00* (2006.01)

(52) U.S. Cl.
USPC ......... 241/19; 241/20; 241/24.16; 241/24.18; 241/24.19; 241/24.2

(58) Field of Classification Search
USPC .......... 44/500–505; 241/19, 20, 24.13–24.15, 241/79.1, 24.16, 24.18, 24.2, 24.19
See application file for complete search history.

(56) References Cited

U.S. PATENT DOCUMENTS

| | | | |
|---|---|---|---|
| 3,524,594 A | 8/1970 | Anderson et al. | |
| 4,077,847 A * | 3/1978 | Choi et al. | 201/21 |
| 4,264,352 A | 4/1981 | Houser | |
| 4,874,134 A | 10/1989 | Wiens | |
| 5,025,929 A | 6/1991 | Carrera et al. | |
| 5,100,066 A | 3/1992 | Frei | |
| 5,184,780 A | 2/1993 | Wiens | |
| 5,361,909 A | 11/1994 | Gemmer et al. | |
| 5,465,847 A | 11/1995 | Gilmore | |
| 5,649,785 A | 7/1997 | Djerf et al. | |

(Continued)

FOREIGN PATENT DOCUMENTS

| | | |
|---|---|---|
| JP | 2003/001298 | 1/2003 |
| KR | 10-1999-0003753 | 1/1999 |

(Continued)

OTHER PUBLICATIONS

Nihot Recycling Technology B.V., "Nihot Drum Separator", 2 pages, (date unknown), Amsterdam, The Netherlands, http://www.nihot.co.uk/fileadmin/nihot/pdf/Nihot_Single_Drum_Separator_01_2011 Eng.pdf, website accessed on Sep. 9, 2013.

*Primary Examiner* — Mark Rosenbaum
(74) *Attorney, Agent, or Firm* — Workman Nydegger

(57) ABSTRACT

Solid waste that includes a mixture of wet organic material and dry organic material can be are separated using mechanical separation to produce a wet organic stream enriched in wet organics and a dry organic stream enriched in dry organics. The separated wet organic stream and dry organic stream are separately converted to renewable or recyclable products using different conversion techniques particularly suited for the separated wet and dry organic streams.

19 Claims, 9 Drawing Sheets

(56) References Cited

U.S. PATENT DOCUMENTS

| | | |
|---|---|---|
| 6,024,226 A | 2/2000 | Olivier |
| 6,117,671 A | 9/2000 | Yilmaz |
| 6,136,590 A | 10/2000 | Kruse |
| 6,168,642 B1 | 1/2001 | Valkanas et al. |
| 6,379,527 B1 | 4/2002 | Vogt et al. |
| 6,903,294 B1 | 6/2005 | Daiku et al. |
| 6,911,149 B2 | 6/2005 | Hansen et al. |
| 7,290,669 B1 | 11/2007 | Hansen et al. |
| 7,431,229 B2 | 10/2008 | Gali |
| 7,452,467 B2 | 11/2008 | Hansen et al. |
| 7,615,155 B1 | 11/2009 | Hansen et al. |
| 7,767,924 B2 | 8/2010 | Jeon et al. |
| 7,810,646 B2 | 10/2010 | Miller et al. |
| 7,942,273 B2 | 5/2011 | Campbell et al. |
| 2002/0184816 A1 | 12/2002 | Philipson |
| 2007/0117195 A1* | 5/2007 | Warner et al. ............ 435/161 |
| 2008/0020456 A1 | 1/2008 | Choate et al. |
| 2008/0169231 A1 | 7/2008 | Hansen et al. |
| 2008/0236042 A1 | 10/2008 | Summerlin |
| 2009/0152173 A1 | 6/2009 | Miller et al. |
| 2010/0201026 A1 | 8/2010 | Dvorak et al. |

FOREIGN PATENT DOCUMENTS

| | | |
|---|---|---|
| KR | 10/0517663 | 9/2005 |
| KR | 10-2006-0059919 | 6/2006 |
| KR | 10-0665251 | 1/2007 |

* cited by examiner

SYSTEMS AND METHODS FOR PROCESSING MIXED SOLID WASTE

CROSS-REFERENCE TO RELATED APPLICATIONS

This application is a continuation in part of application Ser. No. 13/013,707, filed Jan. 25, 2011, which claims the benefit U.S. Provisional Patent Application Nos. 61/298,208, filed Jan. 25, 2010. This application is also a continuation in part of application Ser. No. 13/221,637, filed Aug. 30, 2011 now U.S. Pat. No. 8,398,006. This application is also a continuation of PCT US11/68245 filed Dec. 30, 2011. All of the applications referred above are hereby incorporated herein by reference in their entirety.

BACKGROUND OF THE INVENTION

I. The Field of the Invention

The present invention relates to systems and methods adapted for use in waste recycling and conversion. More specifically, the present invention relates to the recycling and conversion of solid waste derived, for example, from commercial, industrial, or residential refuse.

II. The Related Technology

Commercial, industrial, and residential consumers generate large amounts of throw-away and waste products (i.e., municipal solid waste) that need to be handled and disposed of in an environmentally satisfactory manner. Traditionally, municipal solid waste (hereinafter "MSW") has been disposed of by landfilling or incineration. However, these methods of waste product disposal contaminate the soil, water and air. Environmental restrictions as well as land usage demands for housing have reduced the number of sites available for landfills.

In response, governments and the public have demanded that, wherever possible, recycling systems should be employed to conserve material resources and to reduce pollution problems. Efforts have been made to recover valuable resources such as glass, plastic, paper, aluminum, and ferrous and non-ferrous metals from waste materials. For example, households in many cities are asked to sort their garbage into recyclables (e.g., paper, plastic containers, metal containers and glass containers) and non-recyclables. However, rates of non-compliance and mis-compliance are high. Some people fail to sort their waste at all and other sort it incorrectly, which either shunts recoverable materials into the waste stream or contaminates the recyclable stream with waste materials. Non-compliance and mis-compliance reduce the efficiency of and increases the costs associated with operating recycling systems designed to processed pre-sorted waste.

Some recycling systems attempt to avoid the problems with presorted waste by attempting to recover recyclable materials from mixed waste. However, many of these systems are fraught with the tendency to be highly labor intensive to operate, while offering relatively low recovery rates of recyclables.

The energy balance of many recycling systems is sub-par or, in some cases, negative. Some recycling systems are so inefficient that the processes of recovering, transporting, and recycling the recyclable materials consumes more energy than could be saved by simply landfilling the garbage and making new products from raw materials. In other cases so little of the recyclable materials are recovered that the problems with waste stream disposal go essentially unmitigated.

BRIEF SUMMARY OF THE INVENTION

The present disclosure relates to methods and systems for processing waste that includes a mixture of wet organic material and dry organic material and optionally inorganic material. The systems and methods mechanically separate the mixed solid waste to produce a wet organic stream enriched in wet organics and a dry organic stream enriched in dry organics. Each stream is separately processed to convert at least a portion of each stream into a renewable or recyclable product.

The separated and recovered wet organic and dry organic products constitute high-efficiency feedstock for energy conversion. The wet organic products may be digested in an anaerobic digester to produce biogas or composted for use as a soil amendment. The biogas generated in the anaerobic digester can be compressed or liquefied for use as a transportation fuel and/or can be used to generate electricity and/or heat for use on-site and/or for delivery to the power grid and or converted to liquid fuel. The dry organic material can be recycled and/or used or sold as an organic biomass fuel to produce heat and/or electricity. The inorganic material can be recycled and/or landfilled.

Separating the dry organic material, wet organic materials, and optionally inorganic material maximizes the efficiency of downstream conversion techniques. For example the wet organics can be converted with higher efficiency in an anaerobic digester. Removing non-digestible dry organics and inorganic material prior to loading into a digester increases the volume available for microbial cultures and biogas production. Similarly removing the wet organics and inorganic material from the dry organics increases the efficiency of thermal conversion of the dry organic because less energy is consumed in evaporating water and the burnt material produces less ash. In the case where recyclables are recovered from the dry organics, removing wet organics and inorganic materials reduces burden depths in the sorting process thereby allowing the sorting equipment to function properly and more efficiently and reduces wear and tear on the machinery. In addition, the non-recyclable inorganic fraction can be more easily landfilled because the volume of the landfilled material will be smaller and more concentrated.

The need to efficiently extract multiple types of recyclable materials from variable mixed waste streams is a long-felt but unmet need. The inability of the industry to extract significant percentages of different types of recyclable materials from variable mixed waste streams has resulted in well-known political campaigns throughout much of the world to teach the lay population that it is their responsibility to hand sort recyclables at the time and point of generation and then disposal. Due to natural human behavior, these efforts, while laudable, have not resulted in desired recycle and corresponding diversion rates. The vast majority of recyclable waste materials continue to be poorly recovered and/or utilized. The methods and systems described herein meet this long felt and unmet need by efficiently recovering recyclables using mechanical devices that are arranged and configured to efficiently handle a varied solid waste stream. In addition, traditional curbside residential recycling programs and commercial recycling programs require expensive and polluting separate collection routes and vehicles. Furthermore, once collected by separate vehicles, the materials still need to be separated and the recyclables recovered in traditional Material Recovery Facilities (MRFs). This is highly inefficient and costly.

The systems and methods described herein can handle large volumes of highly variable mixed waste materials. The systems and methods can efficiently extract recyclables from unsorted mixed waste (e.g., black bin MSW), home-sorted recyclable streams where mis-compliance is high (e.g., blue bin MSW), and other types of MSW such as variable commercial solid waste streams from retail establishments, light manufacturing, warehouses, office buildings, etc., and industrial waste streams. The methods and systems described herein can recover significantly larger percentages of different types of recyclable materials and organic materials for conversion into renewable fuels and energy from variable waste streams as compared to known systems. This ability is due in large part to the mechanical separation to divide out the wet organic materials from the dry organic materials and optionally the inorganic materials using mechanical sorters such as shredders, size separators, density separators, and/or dimensional sorters, which creates concentrated, homogenous intermediate waste material streams from which renewable energy and recyclables can be mechanically extracted. Unlike traditional refuse derived fuel plants, the methods and systems of the invention fractionate and spread the waste material sufficiently to prepare the intermediate streams for efficient conversion.

These and other features of the embodiments disclosed herein will become more fully apparent from the following description and appended claims.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only illustrated embodiments of the invention and are therefore not to be considered limiting of its scope. The invention will be described and explained with additional specificity and detail through the use of the accompanying drawings in which.

DETAILED DESCRIPTION

I. Introduction

Figure 1:
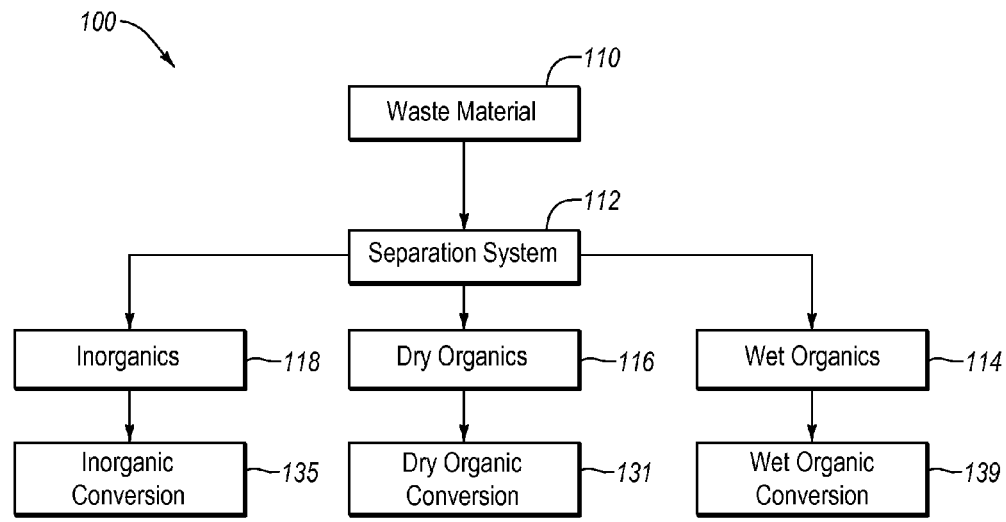
FIG. 1 is a schematic of a mechanized system for converting mixed dry organic and wet organic waste materials (and optionally inorganic materials) into higher value products.

FIG. 1 is a schematic of an integrated waste processing and recycling system 100 that produces renewable energy and/or products from a mixed solid waste material. System 100 includes a source of a mixed solid waste stream 110. The mixed solid waste stream includes at least 10% of a wet organic waste material and at least 10% of a dry organic material and optionally inorganic waste material.

The mixed waste material 110 is mechanically sorted to produce wet organics 114 and a dry organics 116, and optionally inorganics 118. The waste material is processed in a mechanical separation system 112 to produce individual sorted waste fractions that are suitable for conversion into renewable energy and/or products. At least a portion of the dry organics and wet organics are independently processed using separate conversion processes 131 and 139, respectively. Optionally inorganics 118 can be converted into a renewable or recyclable product using inorganic conversion techniques 135. The dry organic conversion 131 is particularly suited for converting dry organic materials to higher value products and wet organic conversion 139 is particularly suited for converting wet organics to higher value products. By concentrating the wet and dry organics into individual fractions, the dedicated conversion processes can be much more efficient compared to performing the same conversion process the mixed solid waste.

Separation system 112 may include components such as conveyors, grinders and/or shredders, screens, air classifiers, magnets, Eddy Current Separators, classifiers, and plastic sorters that together separate the wet organic material from the dry organic material. A mechanical sorter for separating wet organics from dry organics may include a grinding apparatus, size sorting apparatus, and/or a density separator.

Prior to loading waste material 110 into separation system 112, waste material 110 may be manually sorted to remove heavy metal, concrete, and rock items that may damage the separation system 112, bulk cardboard, electronic waste and/or obviously hazardous waste/chemicals. The manual sorting is typically minimal. For example, the manual sorting can be performed by an loader operator of floor sorter while loading waste material into separation system 112 or by one or more line operators that pull obviously valuable items from the waste stream. In a preferred embodiment, less than 40%, 20%, 10% or even less than 1% (by weight) of the mixed waste stream is manually sorted to remove recyclables.

The use of an automated system allows for higher throughput and increased recovery of fuels and/or recyclables. In one embodiment, the throughput of the mechanical sorter of the separation system is at least 2, 5, 10, 20, 50, or 100 metric tons per hour per single line of mixed waste and/or less than 200, 150, 100, or 50 metric tons per hour per single line of mixed waste, or a range of the foregoing upper and lower rates of throughput. The term "single-line" is meant to refer to a single input line that generates single fractional streams of different materials.

Separation system 112 yields a dry organic material 116 having a low moisture content. In one embodiment, the separation yields a dry organic material having less than 30% moisture content, less than 25% moisture content, less than 20% moisture content, or even less than 15% moisture content. Notably these moisture contents may be achieved from the separation system without further drying or blending with dry materials to dilute the moisture content.

Figure 2:
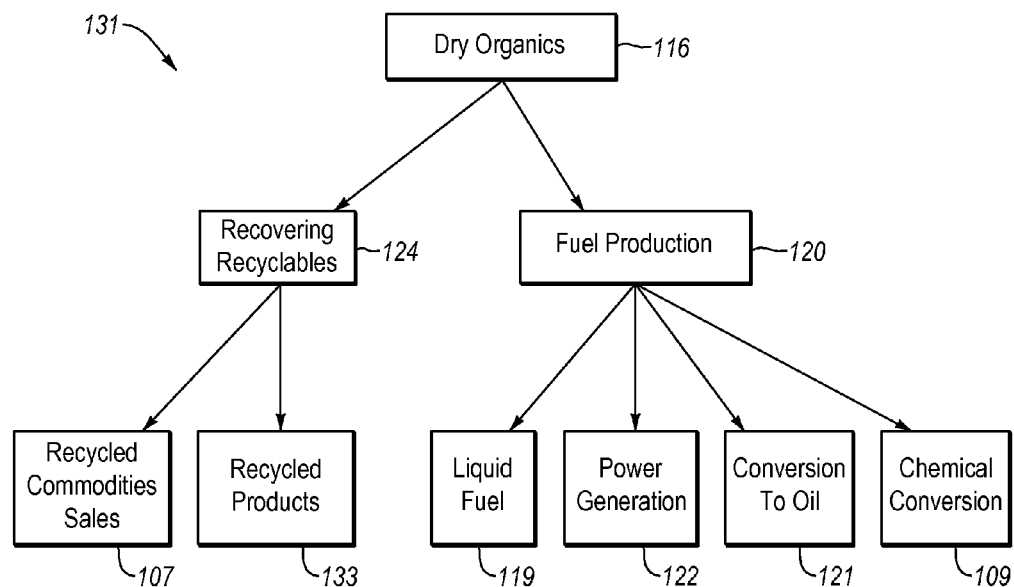
FIG. 2 is a schematic illustrating conversion options for processing dry organics.

With reference to FIG. 2, the dry organics 116 are converted in a first conversion technique 131 to a renewable material. The dry organic conversion can be useful for recovering recyclables (step 124) and/or for fuel production 120. Recovering recyclables 124 can include sufficiently separating materials to produce recycled commodities 107 that can be sold into a market and/or converted into recycled products 133. Fuel production 120 can include conversion of the dry organics to liquid fuel 119, power generation 122, conversion to oil 121, or chemical conversion 109 or some other form of energy.

Even where moisture content is moderately high, the dry organic fuel may be advantageous due to an evenly spread distribution of water. In one embodiment, the separation system 112 produces a dry organic material having less than 5% by mass of particles with a moisture content greater than 40% (more preferably greater than 30% or even greater than 25%). In one embodiment, the dry organic material has less than 3%, 2%, or even 1% by mass of particles with a moisture content greater than 40%, 30%, or 25%.

Figure 3:
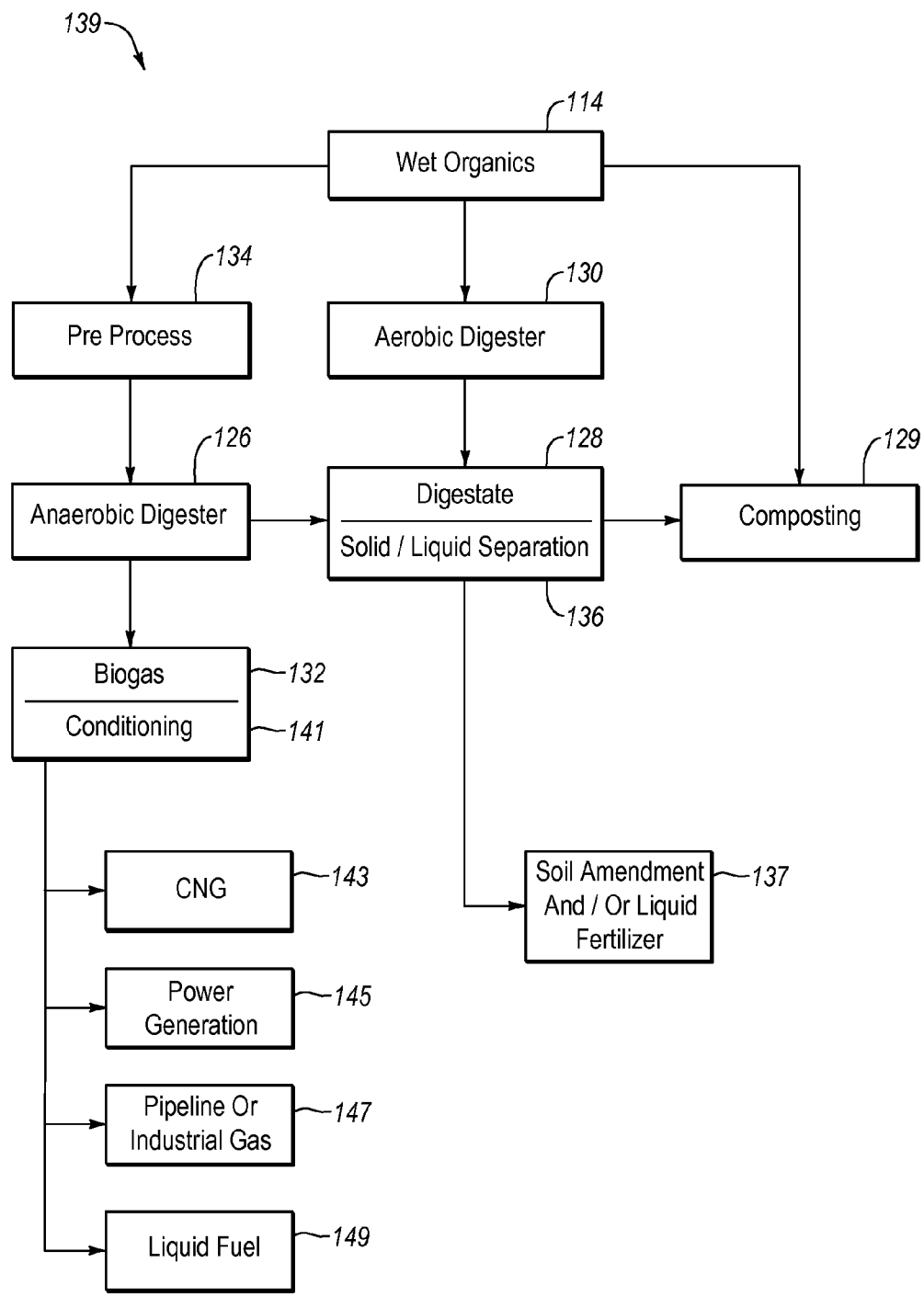
FIG. 3 is a schematic illustrating conversion options for processing wet organics.
Figure 4:
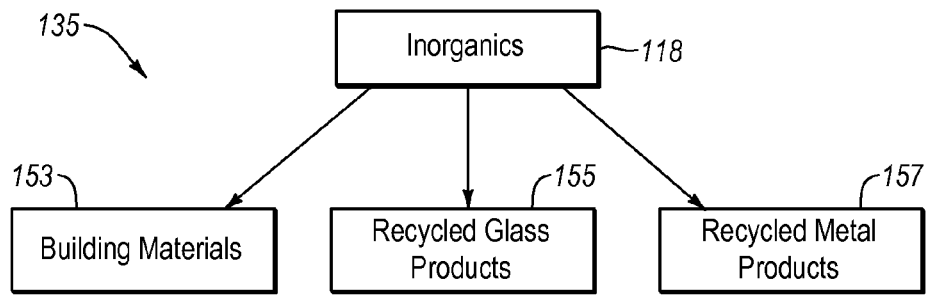
FIG. 4 is a schematic illustrating conversion options for processing inorganics.

While it is desirable to produce a dry organic fraction having the desired moisture content upon separation, the present invention also includes systems in which the dry organic fuel may be dried. In a preferred embodiment, drying is carried out using a waste heat such as waste heat from dry organics power generation system 122 and/or biogas power generation system 145 (FIG. 3). In a preferred embodiment, drying is carried out using only waste heat (i.e., no fuel is burned for the primary purpose of drying).

In one embodiment, the invention relates to maintaining a desired moisture content in the dry organic fraction over time. Maintaining the same moisture content over time can be important for operating a thermal conversion device utilizing the organic fuel. The separation system 112 can be operated so as to minimize variation in the moisture content of the dry organic material 116. In one embodiment, a density classifier can be adjusted up or down in density separation to capture more or less of the wet organic fraction so as to maintain a desired moisture content in the dry organic material. In one embodiment, the dry organic material output from separation system 112 is measured over time and input into a computer configured to control one or more components of separation system 112 to achieve a desired moisture content in dry organic material 116.

With reference to FIG. 3, the wet organics 114 are converted to a renewable material using a second conversion technique 139. The second conversion technique may include anaerobic digestion, which is typically carried out by processing the wet organics 114 in a pre process 134 and digesting the wet material in an anaerobic digester 126. Alternatively wet organics 114 can be processed in an aerobic digester 130 or converted using composting 129. Products from anaerobic digester 126 can include biogas 132 or digestate 128. Biogas 132 may be conditioned or cleaned using conditioning 141 and then converted to compressed natural gas 143. Alternatively, biogas 132 may be used in power generation 145, converted to pipeline or industrial gas 147, or converted to a liquid fuel (e.g., through a Fischer Tropsch process).

Digestate from anaerobic digester 126 or aerobic digester 130 may be further processed using solid/liquid separation to produce a soil amendment and/or liquid fertilizer 137. Solids from digestate 128 may be further improved using composting 129.

Inorganics 118 can also be processed to produce renewable products. The choice to process inorganics 118 tends to depend heavily on the type of material and the proximity of a market for the renewable to the location of system 100. Inorganics can be converted to building materials 153, which can be used in concrete or as a soil amendment. Glass products can be melted and reprocessed to produce recycled glass products 155. Metals tend to have a high value but can be difficult to extract using traditional systems. In contrast, the highly efficient separation system of the invention can recover recycled metal products 157 from materials such as electronics and other hard to separate heterogeneous waste materials.

II. Separation of Wet Organic Waste from Dry Organic Waste

Figure 5:
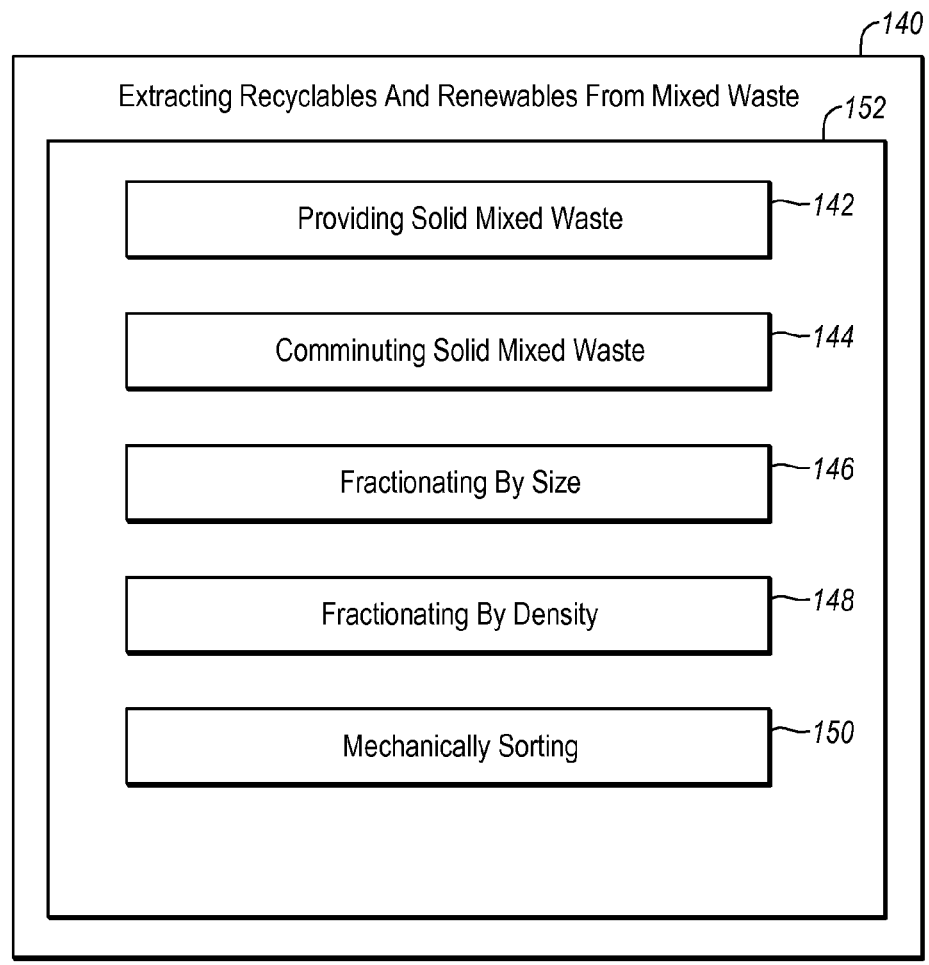
FIG. 5 is a flow diagram illustrating methods for extracting recyclable materials from a mixed solid waste stream.

Mechanical separation is used to separate the components of the mixed waste stream to produce a wet organic stream enriched in wet organics and a dry organic stream enriched in dry organics. FIG. 5 illustrates a flow diagram showing an example process 140 for extracting recyclables and renewables from mixed waste. The steps 152 of separating the wet organics from the dry organics involves all or a portion of the following steps: (i) providing a solid waste stream 142, (ii) comminuting solid mixed waste, (iii) fractionating the waste stream by size 146, fractionating the waste stream by density 148, and mechanically sorting 150.

A. Providing Solid Waste Stream

The waste streams utilized in the methods and systems described herein include a mixture of different types of solid materials. The waste stream includes renewable and or refuse can be utilized and therefore have value. In one embodiment, the mixed solid waste may be Municipal Solid Waste ("MSW") (i.e., trash or garbage). MSW is a type of waste material that includes predominantly household waste with sometimes the addition of commercial and/or industrial wastes collected by a municipality or a contractor hired by a municipality or by commercial and/or industrial businesses within a given area. Commercial solid waste is type of waste such as trash that is generally collected from businesses such as office buildings or business establishments. Industrial solid waste is generally found in heavy manufacturing industries. MSW and commercial waste generally does not include industrial hazardous waste. The mixed waste can be "black bin" waste in which little or no removal of renewable and recyclable material has been performed by the source of the waste or alternatively may be a recycled or "blue bin" waste that includes a mixture of renewable and recyclable waste materials (also referred to as "single stream waste"). The single stream waste may be commercial or residential and may have low or high mis-compliance.

Mixed waste contains a number of components that only have value as a renewable and recyclable material when separated from other components. These renewable and recyclable materials can include a range of plastics; fiber materials, including paper and cardboard; metals, including ferrous metals and non-ferrous metals such as brass and aluminum; glass; textiles; rubber; and wood. Preferably the waste stream includes 1, 2, 3, or more high value materials including, but not limited to one or more of paper, plastic and non-ferrous material.

While even small percentages of these materials may be valuable, separating the renewables and recyclables from each other and other components in mixed solid waste streams is extremely challenging. This is especially true when two, three, four, or more different types of renewables and recyclables need to be separated and recovered.

The methods and systems describe herein include providing a mixed solid waste stream that includes at least 10% of wet organic material and at least 10% dry organic material that is comingled. The mixed waste stream may also include inorganic materials that may be renewable and recyclable or non-renewable and non-recyclable.

The amount of renewable and recyclable materials in the stream, the percentage of the renewable and recyclable material recovered, and the value of the renewable and recyclable material have a significant impact on the economic viability of extracting the renewable and recyclable materials through mechanized sorting (larger values being more desirable).

In one embodiment, the mixed waste stream includes at least 10 wt %, dry organic waste selected from the group of 3-Dimensional typically rigid plastic, film plastic, paper, cardboard, textiles, rubber, and wood. The mixed waste stream may include at least 15%, 20%, 25%, 30%, 40%, 50%, 70% or 90% by weight of a dry organic material and less than 90%, 80%, 60%, 50%, 40%, 30%, 25%, 20%, or 15% by weight of a dry organic material or a range of any of the foregoing upper or lower endpoints.

In one embodiment, the mixed waste stream may include at least 10 wt % wet organic materials selected from the group of food waste (industrial, municipal, or home kitchen waste), animal waste (e.g., manure such as human or other animal manure waste), or green waste (e.g., industrial, municipal or home grass clippings or tree clippings). The mixed waste stream may include at least 15%, 20%, 25%, 30%, 40%, 50%, 70% or 90% by weight of a dry organic material and less than 90%, 80%, 60%, 50%, 40%, 30%, 25%, 20%, or 15% by weight.

The ratio of the wet organics to dry organics will generally depend on the feed stream. In some cases the wet organics may be more concentrated than the dry organics or vice versa. However, in many cases, the wet organic stream may be more prevalent due to food waste. In one embodiment, the wet organic stream is greater by at least 5%, 10%, 15%, 20%, 30%, 50%, or 70% and/or more than 40%, 50%, 60%, or 80% by weight of the wet organics is food waste.

In some embodiments, a significant portion of the waste stream may be a renewable or recyclable material. At least a portion of the waste stream may include a recyclable or renewable material. The mixed waste stream may include at least 2.5%, 5%, 7.5%, or 10% of a recyclable plastic material or less than 60%, 40%, 20% (by weight) or a range of any of the foregoing upper and lower weight percentages of recyclable plastic material.

The mixed waste stream may include at least 5%, 10%, 15%, 20%, 25%, or 30% of a recyclable or renewable mixed paper material or less than 80%, 70%, 60%, 50% or 40% (by weight) or a range of any of the foregoing upper and lower weight percentages of mixed paper material.

The mixed waste stream may include at least 15%, 25%, 35%, of a recyclable or renewable dry organic material and less than 80%, 70%, 60%, 50% or 40% (by weight) or a range of any of the foregoing upper and lower weight percentages of dry organic material. The mixed waste stream may include wet organic waste, dry organic waste, and/or inorganic waste. In one embodiment, the weight percentage of wet organic waste, dry organic waste, and inorganic waste in the mixed waste stream is each (independent of one another) at least 5%, at least 10%, at least 20%, at least 50%, or at least 75% (the sum of the three weight percentages not exceeding 140%).

In one embodiment, the mixed waste stream may include at least 0.5%, 1%, 2%, 3%, 4%, 5% of a recyclable metal or less than 30%, 20%, 15%, 10%, or 5% (by weight) or a range of any of the forgoing upper and lower weight percents of recyclable metal material.

In one embodiment, the mixed solid municipal waste may be an unprocessed municipal waste. For example, solid waste stream may be provided directly from a municipal garbage collection process. Alternatively, solid municipal waste may be partially pre-processed (e.g., by home owners or businesses) to remove a portion of the recyclable and/or recoverable materials. For example, solid municipal waste may be derived from a comprehensive residential or commercial waste stream that contains the remnant materials that exclude source separated materials collected through recycling programs in which a portion of certain recyclables and/or renewables (e.g., mixed paper, newspaper, cardboard, plastics, ferrous and non-ferrous metal and/or glass containers) have been removed (i.e., the MSW may be a post-recycled waste).

In either case (i.e. methods using unprocessed MSW or source separated MSW), the mixed waste may be manually pre-sorted to recover and remove items that are difficult to shred or grind, obviously hazardous, and/or that are particularly large (i.e., easily separated) and have a high recovery value. The presorting may be performed on the facility tip floor, prior to loading waste into the system or may be carried out by personnel on a dedicated presorting line. For example, waste may be metered onto a presorting conveyor where manual labor identifies items to be pre-sorted. Typically pre-sorted items will include items that could damage or cause excessive wear to the shredder or grinder. Examples include automobile engine blocks, structural steel, tire rims, propane tanks, concrete blocks, large rocks, and the like. Hazardous waste is preferably removed before grinding to avoid contamination with other materials in the mixed waste. Examples of obviously hazardous waste include containers of solvents and chemicals, paint cans, batteries, and the like.

Presorting can also be used to recover particularly large and valuable items that are easily picked from the mixed waste stream. Typically the recyclables recovered in the pre-sorting will be items that are several times larger than the burden depth of the process stream such that they are easily visible and efficiently removed manually. For example large cardboard boxes (e.g., corrugated containers), structural metal pieces, and electronic waste (e.g. eWaste) can be recovered in presorting. The percentage of materials in the mixed waste stream described above refer to percentage of the waste stream immediately before it undergoes comminution and/or sizing (i.e., after presort).

As mentioned, the methods described herein allow for materials to be mechanically sorted from municipal solid waste even when the waste includes large percentages of non-recyclable materials. In one embodiment the solid waste stream includes at least 20%, 25%, 35%, 50%, or 75% of one or more low value materials. The low value materials are materials that make separation of the high value materials difficult and that by themselves are generally not economical to separate. In one embodiment the low-value materials can be selected from the group consisting of, wet organics, green waste, food waste, grit, fines less than 1 inch, asphalt, concrete, textiles, wood, rubber, film plastic, PVC, foil, rock, used consumer products, low value glass (glass too distant from a recycler), composite materials (e.g., tennis shoes), other materials typically found in solid waste, and combinations of these. The methods described herein overcome the long felt but unmet need to economically recover (i.e., mechanically sort) all or a portion of the valuable recyclables and/or renewables in these hard-to-handle waste streams. The individual low value materials can be in the solid waste stream in a concentration of at least 5%, 10%, 15%, 20%, or more.

Those skilled in the art will recognize that the composition of solid waste streams varies substantially over short periods of time. Of all the variability found in MSW, there are three constant characteristics in varying degrees or percentages; density, dimension (2-D or 3-D) and moisture content. This invention, in part, uses a variety of equipment that separates by size, density and dimension, and then directs material to equipment that separates or recovers by material type (e.g. resin type for plastic, ferrous metal, non-ferrous metals, glass, paper, etc.). For purposes of this invention, the percentage of a particular type of material within the waste stream can be calculated according to acceptable industry standards such as the 2011 Waste Disposal Guidelines published by the California Department of Resources Recycling and Recovery (Also known as "CalRecycle" and previously known as the California Integrated Waste Management Board), which is hereby incorporated by reference (available at www.calrecycle.ca.gov/wastechar/YourData.htm#Step1 and the links associated therewith). At a minimum sampling of a waste stream shall include analyzing samples of at least 200 lbs and sampling on a plurality of different days, weeks, and/or months.

B. Comminution

Separating the wet organics from the dry organics can optionally include grinding or shredding the mixed waste. Comminution (e.g., shredding or grinding) may improve the efficiency of other processes such as size separation and density separation.

Comminuted waste will have a range of particle sizes. In one embodiment the comminuted waste stream has a upper cut of 16 inches or less, 14 inches or less, 12 inches or less, 10 inches less, or 8 inches or less or a bottom cut greater than 1 inch 2 inch, 4 inch, or 6 inch, or may have a distribution with an upper cut and lower cut of any of the foregoing upper and lower cuts for the comminuted waste. In one embodiment, the ratio of the upper cut to lower cut may be less than 8, 6, or 4.

The size distribution of any particular fractured material generally depends on its material properties. For example, some objects like shipping pallets or tires will be ground or shredded to relatively large particle sizes. In contrast, brittle materials like glass, which tend to shatter, and food waste, which tends to easily shred, will be quite small after comminution.

The shredder or grinder used to comminute the mixed waste stream may include one or more shafts that include a number of cutting heads that that can cut and/or shred incoming waste materials to a selected size. Waste materials may be ground or shredded by turning rotors mounted with cutting blades or knives against a rigid blade housing, they then drop through the grinder or shredder to the screen basket (circular punch plate or finned design screens). Materials having a ground cut size less than a selected size, drop through a screen and move onto the next step in the process. Objects that are too large to pass through the screen are typically recirculated repeatedly through the grinder or shredder until they are ground to a size that can pass through the screen.

A number of solid waste grinders or shredders available in the marketplace are either adapted or can be adapted for comminuting the initial solid waste stream. For example, Vecoplan, LLC of High Point, N.C. makes a number of solid waste shredders that can be incorporated into the system and used in the methods described herein.

Preferably, the comminuted waste from comminuting device is ground or shred to a size of less than 18 inches, 16 inches, 12 inches, 10 inches, or 8 inches and greater than 2 inches, 4 inches, 6 inches, 8 inches, 10 inches, or a range from any of the forgoing upper and lower cutoff sizes. Comminuting the mixed MSW prior to size separation and density separation will increase the separation efficiencies of the density separators.

In the present disclosure, a number of comminuting and/or size fractionation steps are described with respect to methods and systems for the separation of solid waste. Typically each of these steps has an associated size cut-off. Persons having skill in the art will appreciate that fractionated materials typically exhibit a distribution of particles. The distribution of any particular fraction will often include an insignificant number of particles above or below the cut-off. Unless otherwise specified, an upper cut-off number (e.g., 16" or less, 12" or less, 8" or less, the upper range of an 8" to 2" over fraction) generally means that about 90% of the particles in the particular fraction have a size of less than the cut-off number, while about 10% of the particles in the particular fraction will be larger than the upper cut-off size. Unless otherwise specified, a lower cut-off number (e.g., the lower range of an 8" to 2" over fraction) generally means that about 90% of the particles in the particular fraction have a size of larger than the cut-off number, while about 10% of the particles in the particular fraction are smaller than the lower cut-off size. In some embodiments the cutoffs can be more efficient than 90% and 10%. For example, the upper cut-off number for a particular fraction 95% or 99% of the particles can be less than the upper cutoff number and/or less than 5% or less than 1% of the particles in the fraction can be smaller than lower cut-off size. The particular cutoff numbers relate to the particular fraction, not the entire distribution. Depending on the waste stream, a significant percentage of the feed waste stream can be smaller than the lower cut-off number and/or larger than the upper cut-off number, regardless of the efficiency of the separation equipment.

C. Size Separation

The comminuted waste may be conveyed to a size separator that fractionates the mixed waste by size to produce two or more sized waste stream (e.g., at least an over fraction and an under fraction).

The sizing may be carried out to produce sized waste streams with a particular desired particle size distribution to facilitate density separation and to produce intermediate streams enriched in particular recyclable or renewable materials. Those skilled in the art will recognize that the comminuted waste stream can be analyzed to determine size cutoffs in which the fractions of the stream separate different types of materials into different streams while concentrating similar types of waste into somewhat concentrated streams. In addition, the sized waste streams may be optimized for density separation by creating sized waste stream with a narrow distribution of particles.

In one embodiment, the sized waste streams may have a size distribution with a ratio of small particles to large particles of less than about 10 (i.e., the ratio of the upper cut-off to the lower cut-off has a ratio less than about 10), more preferably, less than about 8, 6, or 4. An under fraction from size separation may have a top size cut-off of less than about 6 inches, 5, inches, 4 inches, 3 inches, or two inches and greater than 0.5 inch, 1 inch, 2 inch, or 3 inch, or a range within any of the foregoing upper and lower values for the top size cut. The upper fraction may have an upper size cutoff less than 16, inches, 12 inches, 10 inches, 8, inches or six inches and a lower size cutoff greater than 2 inches, 4 inches, 6, inches, or 8 inches or a range within any of the foregoing upper and lower cutoffs.

Suitable examples of a size separator that can be used in the present method include a disc screen separator with rubber or steel discs, a finger screen separator, a trommel screen separator, a vibratory screen separator, a waterfall screen, oscillating screen, flower disc screens, and/or other size separators known in the art.

A disc screen employs a series of rolling shafts having a series of attached discs with spaces between the discs that objects can fall through. The rolling of the shafts creates a wavelike action that agitates the incoming material as it is conveyed forward. This agitation releases smaller materials through the screen openings and is accomplished without vibration or blinding. The disc screen design greatly reduces the possibility of jamming or seizing during operation. Trommels, vibratory, or finger screens, waterfall screens, oscillating screens, flower disc screens, and/or other size separators known in the art also accomplish the same type of size separation objective, while using somewhat different engineered designs. Various size separators useful in the invention are commercially available through many different manufacturers worldwide. For example, disc screens, trommel screens, vibratory screens and waterfall screens are available from Vecoplan, LLC of High Point, N.C.

D. Density Separation

One or more of the sized waste streams may be separated by density to produce intermediate waste streams that are individually enriched in wet organics, dry organics, and/or particular renewable materials. Although not required, the density separation is preferably performed in a separate apparatus downstream from the size separator. Downstream density separation allows distinct density separators to be used on individual sized fractions, which allows the individual density separators to be configured for particular materials and streams. The density separator units may be calibrated to provide separation between particular materials in the mixed waste stream. Density separation can be used to separate different types of materials such as wet organics, dry organics, and inorganic materials, thereby enriching one or more particular intermediate streams in one or more different types of recyclable and/or renewable materials.

In mixed municipal waste streams, inorganic waste, wet organic waste, and dry organic waste often exhibit densities within particular ranges. For example, dry organics tend to have a density of greater than 1.0 lbs/cubic foot and less than about 12 or 15 lbs/cubic foot; wet organics tend to have a density greater than 8, 10, or 12 lbs/cubic foot and less than about 60, 80, or 140 lbs/cubic foot; inorganic materials tend to have a density greater than about 80 or 140 lbs/cubic foot. Thus, by setting the density separators accordingly, the wet organic, dry organic, and inorganic fractions may be separated based on density. Similarly, particular types of recyclable and/or renewable materials such as wood and textiles will often fall within a certain density range and can be selectively enriched in an intermediate waste stream. While the foregoing densities are useful for many municipal waste streams, those skilled in the art will recognize that the teachings provided herein can be used to analyze any waste mixed solid waste stream and determine density cutoffs that will generate intermediate waste streams enriched in recyclable or renewable materials.

In some embodiments, a series of density separators can be used to further fractionate the intermediate waste streams. In downstream density separators, the density cutoff is selected to fractionate either the lower or the upper fractions received from the upstream density separator. Additional size separation may also be carried out on density separated streams. Size and density separation are carried out until the intermediate stream is sufficiently enriched and homogenous in a particular recyclable or renewable material to allow efficient extraction of the recyclable or renewable material using mechanized sorting equipment.

Figure 6:
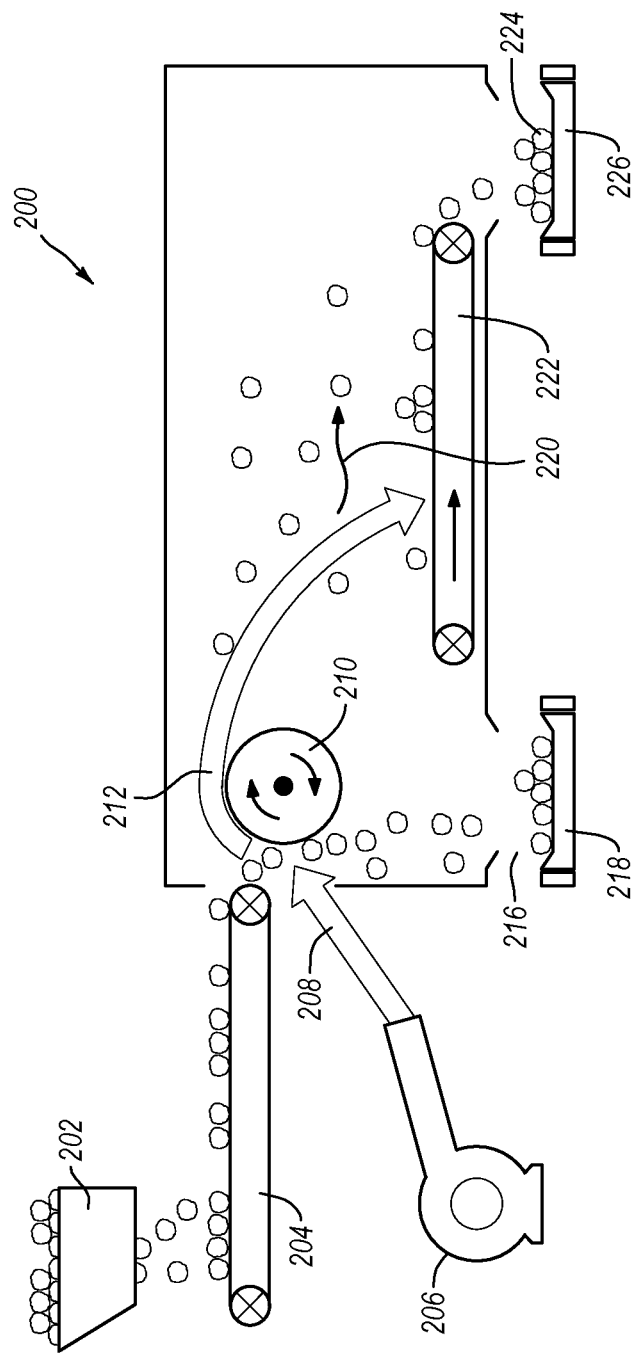
FIG. 6 illustrates a cut-away view of an air drum separator adapted for use in the system for separating solid waste by density, according to one embodiment of the present invention.

Referring now to FIG. 6, an example of a density separation unit that is adapted for separating municipal solid wastes by density is shown. FIG. 6 illustrates an air drum separator 200. The air drum separator 200 includes an input conveyor 204, a blower 206, a rotating drum 210, an output conveyor 222, a heavy fraction conveyor 218, and a light fraction conveyor 226. Mixed density wastes 202 are fed in on the input conveyor 204. As the waste material 202 is fed in, it drops off the end of the conveyor 202 where the wastes 202 encounter a stream of moving air 208 from the blower 206.

The heavy fraction 216 is separated from the mixed waste material 202 by virtue of being too heavy to be lifted by the airstream 208. The heavy fraction thus falls down in front of the drum 210 and falls on to the heavy fraction conveyor 218. In contrast, the lighter wastes are lifted up by the airstream 208 and carried over the rotating drum 210 and carried forward either by the airflow 220 or by the conveyor 222. The light fraction 224 drops off the end of conveyor 222 and onto the light fraction conveyor 226. These machines are highly adjustable to alter the weight density separation coefficient, as desired.

The relative density of the heavy fraction 216 and the light fractions 224 can be adjusted by controlling the airflow through the air drum separator 200. The velocity of the airflow and the volume of air passing through the drum separator 200 can be controlled either by increasing or decreasing the velocity of fan 206 or by opening or closing valve 212. In general, opening valve 212 and/or increasing the velocity of the fan 206 will carry heavier objects over the drum 210 such that the light fraction will have a higher average mass. Likewise, closing valve 212 or lowering the velocity of the fan 206 will cause the heavy fraction 216 to have a lower average mass and the light fraction 224 will have a lower average mass because only the lighter objects will be carried over the drum 210. Density separators suitable for use in the present invention include, but are not limited to air separators available from Westeria Fördertechnik GmbH, Ostbevern, Germany. While the particular example illustrated in FIG. 6 may be preferred in some embodiments, other separators can be used, including density separators that do not include drums (e.g., gravity/air separators, windshifters, windsifters, air knifes, etc.).

Density separators like those illustrated in FIG. 6 work best when the ratio between the largest and smallest objects being fed into the density separator is relatively narrow. Accordingly, it is preferable that the ratio of the largest to smallest objects that are fed into the density separators in the methods and systems described herein be about 12 to 1, about 10 to 1, about 8 to 1, 6 to 1, or about 4 to 1. Most preferably, the ratio of the largest to smallest objects that are fed into the density separators in the methods and systems described herein is about 6 to 1 (i.e., where the ratio of the top-cut to the bottom cut are in the foregoing ratios). In one embodiment, the methods and systems of the present invention are designed to provide waste materials to the density separators with particles size ratios within these approximate ranges.

E. Metering To Control Flow Rates and Burden Depth

Optionally, the methods can also include metering the sized waste streams and intermediate waste streams throughout the system to achieve a desired mass flow and burden depth. In one embodiment, the comminution apparatus, size separator, density separator, and/or mechanized sorters are separated by one or more conveyors that have variable speed controls. The variable speed control can be set to optimize the mass flow through the comminution apparatus, size separators, density separators, and/or mechanized sorters to optimize the quantity, purity, and/or value of the recyclable or renewable materials being recovered from the overall system by ensuring a metered and evenly distributed presentation of material to the individual devices. One or more sensors positioned upstream, downstream, or within the one or more of the components of the system can be used to monitor the separation efficiency, effectiveness, separation purity and/or rate of recovery of the recyclable or renewable materials. These values can then be used to optimize or maximize one or more parameters of the system such as recovery quantity, purity, and/or value of the recyclable or renewable materials recovered. Examples of sensors that can be used to control the flow rate of the waste streams include level sensors such as, but not limited to optical sensors and/or ultrasonic sensors that measure the height of material building up on a conveyor and/or upstream of a metering device and/or that measure open space on a belt. A belt, metering device, or other piece of equipment can be sped up or slowed down using the sensor data to ensure that a flow rate or desired burden depth is achieved on a belt or in or through a piece of processing equipment (e.g., size separators) and/or any other portion of the system described herein. Other sensors include mechanical switches that are physically actuated by the waste stream building up beyond a desired level (e.g., height), which actuates the mechanical switch to provide a signal that can then be used to regulate flow or burden depth. The speed of all metering equipment including; walking floors; conveyors; metering drums; shredders and grinders; air drum separators; screens of all types; vibratory feeders; metering feeder bins; load levelers; and other such devices can be controlled and adjusted via control systems and other devices in order to properly meter material through all portions of the invention. In some embodiments, the metering can be critical to obtain the desired high recovery and purity of recyclable or renewable materials from mixed solid waste.

The systems and methods can include using a plurality of sensors and metering the flow or depth burden of waste material conveyed to a plurality of sorting apparatuses. Although not required, it is preferable that each sorting apparatus have a sensor associated therewith and that the sensor be used to independently control metering of the two or more sorting apparatuses. For example, a level sensor or flow sensor can be positioned near an inlet of any combination of 3-dimensional sorter, optical sorter, eddy current separator, or the like.

III. Conversion of Renewable Materials

The separated dry organic stream and the wet organic stream are separately converted to a renewable product using first and second conversion techniques, respectively. Any number of conversion techniques can be used to process any number of separated enriched intermediate waste stream produced in the separation system 112 (FIG. 1). The first and second conversion techniques are different techniques, which allows the techniques to be selected to be more suitable for converting wet or dry organics, respectively, as compared to a single conversion technique. For example, dry organics may be converted to refuse derived fuel with less energy consumption than materials that include wet organics and must be dried and wet organics can be converted to biogas in an anaerobic digester more efficiently without the dry organics and inorganics.

A. Conversion of Dry Organic Material

Any number of dry organic conversion techniques may be used to convert the dry organic fraction to a renewable product such as a refuse derived fuel (RDF) or recyclable material. Examples of suitable conversion techniques include plasma arc thermal conversion, gasification, pyrolysis, biomass thermal conversion, plastic to oil conversion, biogas to liquid fuels (e.g., Fischer Tropsch), refuse derived fuels, chemical conversion processes (e.g., PETE plastics to terephthalate)

In one embodiment the dry organic material can be converted to a refuse derived fuel by processing the dry organic waste to have a particular desired moisture content and BTU value. In one embodiment, the dry organic material may have a BTU value in a range from about 4000-15,000, more specifically about 5000-10,000, and even more specifically about 6000-8,000 and a moisture content as stated above.

The refuse derived fuel (RDF) may be compacted to allow it to be shipped and/or properly combusted in a biomass boiler. Typically the compacted dry organic material 116 can have a density in a range from about 0.5 lb/ft$^3$-50 lb/ft$^3$, more specifically about 1 lb/ft$^3$-30 lb/ft$^3$, even more specifically about 2 lb/ft$^3$-20 lb/ft$^3$, and most specifically about 3 lb/ft$^3$-10 lb/ft$^3$.

The RDF fuel may be compacted to form flakes or pellets and may be by any means to a site where RDF fuel is used such as, but not limited to a cement plant where the dry organic material may be used to heat a kiln for manufacturing cement.

In a preferred embodiment, the dry organic material is not pelletized and is used on site in one or more conversion technologies such as thermal conversion or electricity production. Where power is produced, the electricity can be used on site or connected to a local power grid. Because the power is generated locally, the electrically power is more valuable since very little power will be lost in transmission.

In one embodiment, the dry organic material 116 can be used as a fuel in a biomass boiler to generate steam and drive a steam turbine to generate electricity. An example of a biomass boiler is described in US Patent Application publication 2009/0183693 to Furman, which is hereby incorporated by reference.

In one embodiment, the biomass boiler can be configured to be fired using a fluidized feed. The dry organic material can be relatively light and easily fluidized for good burning within a fluidizing biomass boiler. The use of this type of biomass boiler in combination with on-site power generation saves compacting and/or pelletizing costs, produces an efficient burn in the boiler, allows local use of the electricity and waste heat, thereby maximizing the caloric value of the dry organic material and minimizing carbon emissions.

The dry organic material may be used in a gasification process. Gasification may be achieved by reacting the dry organic waste at high temperatures (>700° C.), without combustion, with a controlled amount of oxygen and/or steam to produce syngas. The syngas can be further utilized to produce fuels. Several different gasification processes are available for use with dry organic waste. Examples of suitable gasifiers include co-current fixed bed gasifiers, fluidized bed reactors, entrained flow gasifiers, and plasma gasifiers.

In one embodiment the dry organic material can be converted to a high value chemical compound (i.e., other than a hydrocarbon fuel). For example plastics and rubber can be converted to polystyrenes by catalytic cracking with two-step distillation; polyolefin material can be formed by catalytic cracking and polyethyleneterephtalate can be created from PETE by solvolysis. Conversion techniques for producing these high value chemical compounds are available from Gossler Envitec GmBH (Germany).

In yet another embodiment separated plastics such as film plastics can be converted to liquid fuels through a plastic to fuels conversion techniques known in the art (usually catalytic processes and/or pyrolytic processes). Components of the dry organic stream can also be converted to biogas through digestion. For example, paper products may be pulped and then digested by anaerobic digestion to produce biogas, which can be combusted or converted to a liquid fuel using a suitable process such as Fischer Tropsch.

Wet organics may be converted in part using mechanical biological treatment in which the wet and dry organics are encapsulated and allowed to give off water to reduce the water content. The dried organic waste can then be further processed using one or more other conversion techniques.

The methods described herein also include extracting a plurality of recyclable materials or renewable materials from the intermediate waste stream using one or more mechanized sorting apparatuses. The particular mechanized sorting apparatus used depends on the particular recyclable material or renewable material to be extracted.

With reference again to FIG. 2, method 140 includes (i) in a first step 142, providing a mixed waste stream including recyclable materials such as paper, plastic, and metal (particularly non-ferrous metal); (ii) in a second step 144, comminuting the mixed waste stream; (iii) in a third step 146 fractionating the mixed waste stream by size to produce a plurality of sized waste streams; (iv) in a fourth step 148, fractionating at least a portion of the sized waste streams by density to produce a plurality of intermediate waste streams individually enriched in one or more of the recyclable materials; (v) in a fifth step 150, individually sorting the plurality of intermediate waste streams using one or more sorting apparatuses to produce recyclable products such as, but not limited to recycled paper products, recycled plastic products, and/or recycled metal products. Optionally the method can include metering and/or spreading the sized waste streams throughout any or all portions of process 140 to control mass flow and/or burden depth. In one embodiment, the sorting apparatus may be a dimensional sorter such as a 2-Dimensional-3-Dimensional sorting apparatus. Examples of 2D-3D sorters include ballistic separators and/or screens configured to separate two-dimensional items from three-dimensional items. Two or more ballistic separators and/or screens can be used in series or parallel. The dimensional separators can be used to recover one or more materials that are comingled with another material having a similar density, but having substantially different dimensional properties (other than size). For example, in one embodiment, the 2D-3D separator may be used to separate rigid plastics (which tend to be three dimensional) from plastic film and/or paper, which are generally two-dimensional and flexible. Two-dimensional plastics including films and rigid materials generally have a thickness less than ⅛ inch. Thus, the 2-dimensional materials are considered 2-dimensional because their thickness is much less than their length and width (e.g., 10 times or 140 times less). In addition or alternatively, a 2D-3D separator can be used to separate wood (which tends to be more three dimensional) from textiles (which tends to be more two dimensional). Ballistic separators can also separate materials into rigid and flexible categories.

Another mechanized sorting apparatus that can be used is an optical sorter. The optical sorter may be configured to separate film plastics from paper or separate different types of plastics from one another. For example an optical sorter can be configured to recover HDPE and/or PETE from an intermediate waste stream. One or more optical sorters may also be configured to recover #1-7 plastics and/or to remove and/or recover PVC plastics. The optical sorters may also be used to sort glass from an intermediate stream enriched in small inorganic particles. There are many types of optical sorter technologies, including, but not limited to; Near Infrared (NIR), camera color sorters, X-Ray, etc.

Optical sorters can scan the intermediate waste stream and determine whether the material being analyzed is a particular type of plastic, paper, or glass. The optical sorter, upon detecting a particular material, uses air directed through nozzles to eject the targeted/identified material to produce one or more recycled products such as recyclable PETE, recyclable HDPE, recyclable film plastic, recyclable #3-7 plastic and/or recyclable paper products.

Any optical sorter known in the art can be used. For example, in one embodiment the optical sorter can operate by scanning the intermediate waste stream in a free fall using a camera sensor. The camera sensor detects the material and then air jets may quickly eject the material while in free fall. There are also optical sorters that utilize near infrared, X-Ray and other scanning technologies to separate targeted materials from mixed streams. Any number of optical sorters can be used in series or parallel. Manufacturers of optical sorters include TiTech Pellenc, MSS, NRT and others.

B. Conversion of Wet Organic Material

The wet organic fraction may be processed in one or more conversion techniques that are most suitable for materials with high moisture content (e.g., greater than 25 wt % or 30 wt %) water. Suitable conversion techniques for the wet organic stream include wet or dry digestion including anaerobic digestion, aerobic digestion, and compositing.

With reference again to FIG. 1, separation system 112 produces a wet organic material 114 that is digested in anaerobic digestion 126. Separation system 112 can use any anaerobic digestion including complete mix, plug-flow, and/or up-flow anaerobic digestion. In a preferred embodiment, anaerobic digestion system 126 includes an up-flow anaerobic digester and most preferably the upflow anaerobic digester system is an induced blanket upflow anaerobic digester. Induced upflow anaerobic digesters include a horizontal septum that increases the retention of solids and bacterial and decreases the hydraulic retention time needed to digest organic solids.

In one embodiment, the hydraulic retention time of the anaerobic digester is less than 20 days, more preferably less than 15 days, and most preferably less than about 10 days. Preferably the anaerobic digestion system 126 includes a plurality of individual tanks that allow for maintenance without interrupting overall service. Preferably the anaerobic digester includes methanogenic and acidogenic bacteria in a single tank.

A description of suitable microbial digestion systems that can be used to digest the wet organic waste product produced in the current method can be found in U.S. Pat. No. 7,615,155 entitled "Methods for removal of non-digestible matter from an upflow anaerobic digester," U.S. Pat. No. 7,452,467 entitled "Induced sludge bed anaerobic reactor," U.S. Pat. No. 7,290,669 entitled "Upflow bioreactor having a septum and an auger and drive assembly," and U.S. Pat. No. 6,911,149 entitled "Induced sludge bed anaerobic reactor," and in U.S. Pat. Pub. No. 2008/0169231 entitled "Upflow bioreactor with septum and pressure release mechanism," the entireties of which are incorporated herein by reference.

To provide optimal digestion in digester system 126, a preprocessing digester infeed system 134 may be used as discussed above with regard to FIG. 3. Digester in-feed 1134 may include a grinder or shredding apparatus for reducing the particle size of the wet organic material. In one embodiment the particle size is reduced to less than about 1 inch, more preferably less than ¾ inch, and even more preferably less than ½ inch. Digester infeed 134 may also include increasing the temperature of the wet organic material to achieve a desired temperature near or within 2-10° C. above the operating temperature of the digester. In addition, water may be added to the organic material to achieve a desired solids concentration. In one embodiment, the temperature may be mesophilic or thermophilic. In one embodiment, the temperature is in a range from about 110° F. to about 180° F., more specifically about 120° F. to about 150° F. These temperatures can be achieved using waste heat from on-site power generation and/or from operating a furnace using on-site organic fuel and/or biogas. The heating can be to a component of the in-feed system 134 or directly to the anaerobic digester.

In one embodiment, water added to the wet organic material is obtained from an effluent from anaerobic digester system 126. The digester infeed 134 can produce a mixture of wet organic material having a solids content in a range from about 5% to about 40%, more specifically a range from about 10% to about 35%, about even more specifically about 15% to about 30%.

As mentioned above with respect to FIG. 3, anaerobic digestion system 126 or aerobic digestion system 130 may produce a compost-like product (i.e., digestate 128). Digestate 128 may be dewatered or dried directly or further cured through aerobic composting 129 and/or otherwise processed into a high nutrient soil amendment 137. In a preferred embodiment, digestate 128 has reduced pathogens and/or reduced seed content and should be as free as possible of inorganic materials such as glass and plastic. High-quality digestate can be produced by using thermophilic temperatures in anaerobic digestion system 126, coupled with extensive separation processes 112 and digester infeed preprocess 134 to remove undesirable inorganic materials. Digestate 128 may be dewatered using mechanical methods 131 and dried using the waste heat from biogas power generation system 145 and/or dry organic power generation system 122. In this embodiment the exhaust from combustion can directly heat the digestate or the exhaust may indirectly heat the digestate through the use of a heat exchanger. Alternate drying methods include aerobic composting 129, solar drying, or air drying.

As mentioned, anaerobic digestion system 126 produces biogas 132, which can be can be conditioned using a biogas conditioner to remove impurities and/or to increase the concentration of hydrocarbons. Biogas conditioning 141 can include removing hydrogen sulfide, carbon dioxide, water, and/or other constituents commonly found in biogas. Gas conditioning can be carried out by adsorbing undesired constituents onto an adsorbent such as zeolite.

Conditioned biogas 132 can be processed into a liquid or compressed fuel 131. Typically biogas 132 is compressed in a series of compressors to achieve a desired pressure for use in transportation fuel. Compressed and conditioned biogas 132 can be used on-site to power equipment that traditionally runs off of diesel fuel. Alternatively, conditioned and compressed biogas 132 may be sold or transported for use in conventional compressed natural gas applications. In yet another embodiment, conditioned biogas 132 may be liquefied using compressors and/or refrigeration. Liquefied biogas can be sold or transported for using conventional liquefied natural gas applications. Conditioned biogas 132 can also be converted into bio-diesel using a Fischer Tropsch process.

Conditioned biogas 132 may also be burned to produce heat and/or electrical power in biogas power generation system 145. Biogas power generation system 145 can use power generation systems known in the art for combusting methane to produce electrical power. Power generation system 145 can use a micro-turbine or conventional internal combustion engine coupled with an electrical generator and/or a thermal oxidizer coupled with a steam generator. Conditioning biogas 132 can improve the combustion properties of biogas 132 and power generation system 145. However, where the power generation system 145 is designed to burn low BTU biogas and/or biogas including gases such as hydrogen sulfide, biogas 132 can be used in power generation system 145 without gas conditioning.

Examples of other techniques for converting wet organic waste include composting in which the wet organic material is allowed to degrade in the presence of oxygen to produce a compost with aerobic conditions. This technique is energy intensive and not preferred where it is desirable to obtain biogas.

Wet organics may also be processed in dry digestion in which the wet organics may be placed in a digester alone or in conjunction with other dry organics or inorganic materials through which moisture under low oxygen conditions percolates through the material to create anaerobic conditions. Dry digestion produces a biogas that can be collected and combusted for power generation or converted to a liquid fuel.

C. Recovery of Inorganic Material

In one embodiment, the intermediate waste stream may be enriched in metal, including a ferrous metal and/or a non-ferrous metal. To extract a non-ferrous metal an eddy current separator can be used. The eddy current separator can recover non-ferrous metals such as aluminum, brass and copper. Alternatively, or in addition, the metals may include ferrous metal and one or more magnetic separation devices can be positioned throughout the system and configured to collect ferrous metal. Examples of magnetic separators include drum magnets, cross-belt magnets, head pulley magnets, and the like. Optical sorters, stainless steel sorters, infrared sorters, camera sorting machines, induction sorters, metal detection systems, X-ray sorters and the like can be used to separate different types of metals from one another, to produce a recyclable product. The recyclable metal products produced in the methods and systems described herein can be selected from the group including non-ferrous recyclable products such as aluminum, brass, and copper and/or other metals such as iron and/or stainless steel.

The mechanical fractionating and sorting of the systems and methods described herein are particularly useful for extracting high value waste materials such as non-ferrous metals, as well as paper and plastic. In prior art systems these items have been particularly difficult (or practically impossible) to extract and/or sort from mixed solid waste. Conventional systems often cannot extract a significant portion of paper, plastics and/or non-ferrous metals because these materials cannot be extracted using a magnet. It is well-known to use magnets in traditional mixed waste processing systems. Magnets are sufficiently inexpensive and can be used in multiple locations within a system to make their use economically viable even when the magnet only extracts a small percentage of the ferrous material. However, recovering even ferrous metal from mixed solid waste is extremely difficult and inefficient due to the multitude and variety of materials found in mixed solid waste. The typical condition of mixed solid waste, as it is purged from the collection vehicles and/or transfer trailers, is such that a simple magnetic device would likely get a very small percentage, under 20%, of the available ferrous metal contained in the mixed solid waste stream and any metal recovered in such a fashion would be highly contaminated by other materials found in mixed solid waste that would be caught between the magnet's surface and the ferrous metal object that was attached (e.g. paper, plastic, etc.). In contrast, materials such as recyclable plastics, paper, and non-ferrous metals (e.g. brass) are often not extracted from mixed waste because the sorting equipment for these particular materials cannot handle the waste streams as configured in these systems. Despite the fact that non-ferrous metals and many sorted recyclable plastics typically have a value 5-15 times as much as ferrous metals, the industry usually only uses mechanical means to extract ferrous metal from mixed solid waste. Furthermore, recovery of these higher value recyclables such as paper, plastics and non-ferrous metals is plagued by the same usual conditions of mixed solid waste, in that such recyclables are so thoroughly mixed and hidden within the large variety of other non-recyclable items found the mixed waste stream (e.g. organics, inert materials, wood, textiles, fines, etc.). Additionally, a large portion of mixed solid waste, especially from residential collection routes and multi-family dwellings is deposited in plastic bags and discarded. Manually opening bags of trash that would somehow be picked from mixed solid waste and the subsequent sorting and recovery of any liberated recyclables, would be cost prohibitive in all but the most underdeveloped Countries. Finally, the highest valuable recyclable commodities/materials (e.g. PETE plastic, HDPE plastic, #3-7 plastic, aluminum cans, stainless steel, copper, brass, mixed non-ferrous metals) are generally found to be comprised of very small percentages of between 0.1% to 4%, on an individual material basis, relative to the overall mixed solid waste stream. Without most or all of the components described herein (e.g., preparation, sizing, metering, homogenizing and sorting), extracting these high value recyclable materials from materials with such low available percentages within the mixed waste stream is nearly impossible to do in an economically viable method. The methods described herein offer novel, efficient and high throughput solutions to this long-standing challenge in the waste processing industry.

D. Recovery Rates Of Recyclable and Renewable Materials

The present invention is particularly advantageous for recovering the majority of one or more different types of recyclable and renewable materials present in a mixed solid waste stream. The methods and systems are particularly useful where high value recyclables are present in very low concentrations. The systems and methods allow processing of mixed waste stream to metaphorically speaking "pick the needle out of the haystack." In one embodiment, the mixed waste stream may include at least one type of recoverable material at a concentration less than 15%, less than 10%, less than 5%, or even less than 1%, where the system or method is configured to recover at least 50%, at least 70%, at least 80%, or even at least 90% of the particular recoverable material.

In addition, the methods and systems as described herein may recover at least 25%, 50%, 75% or 90% of the recyclable metal in the waste stream (by weight) as recyclable metal product having a purity suitable for sale to a merchant of recyclable metals.

The process may recover at least 25%, 50%, 75% or 90% of the recyclable plastic materials in the mixed waste stream (by weight) to yield a recyclable plastic product having suitable purity for sale to a merchant of recyclable plastic products.

The process may recover at least 25%, 50%, 75% or 90% of the recyclable mixed paper products in the mixed waste stream (by weight) to yield a recyclable mixed paper product having a purity suitable for sale to a merchant of recyclable mixed paper.

The process may recover at least 25%, 50%, 75% or 90% of the recyclable dry organic materials to produce one or more (e.g., 1, 2, 3, 4, or more) recyclable or renewable dry organic products. The dry organic products may be selected from the group of mixed paper, 3-D plastics, film plastics, textiles, and wood.

The comminuting, size separation, and/or density separation may be used to produce homogeneous recycle streams that are sufficiently free from contamination to be recycled or used without further separation from other types of components present in the mixed waste and/or that are marketable as a recyclable product.

The various renewable materials and products can be used on site or off site from the separation system to produce renewable products such as plastic bottles, metal parts, energy, and/or heat for carrying out any manufacturing process known in the art to utilize renewable energy and products.

IV. Systems for Separating Mixed Solid Waste

Figure 7:
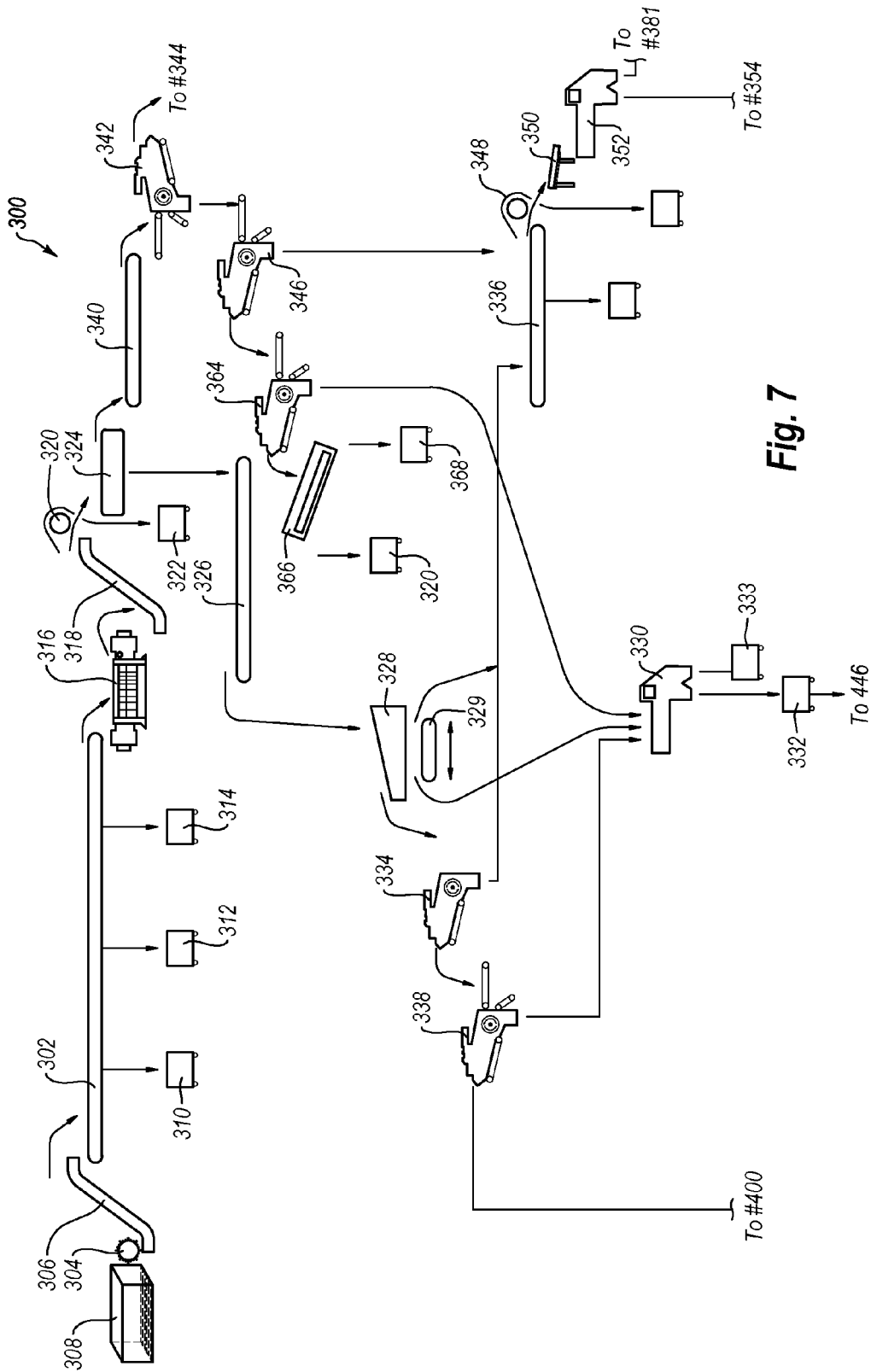
FIG. 7 is a flow diagram illustrating a system for separating solid waste, according to yet another embodiment of the present invention.
Figure 7:
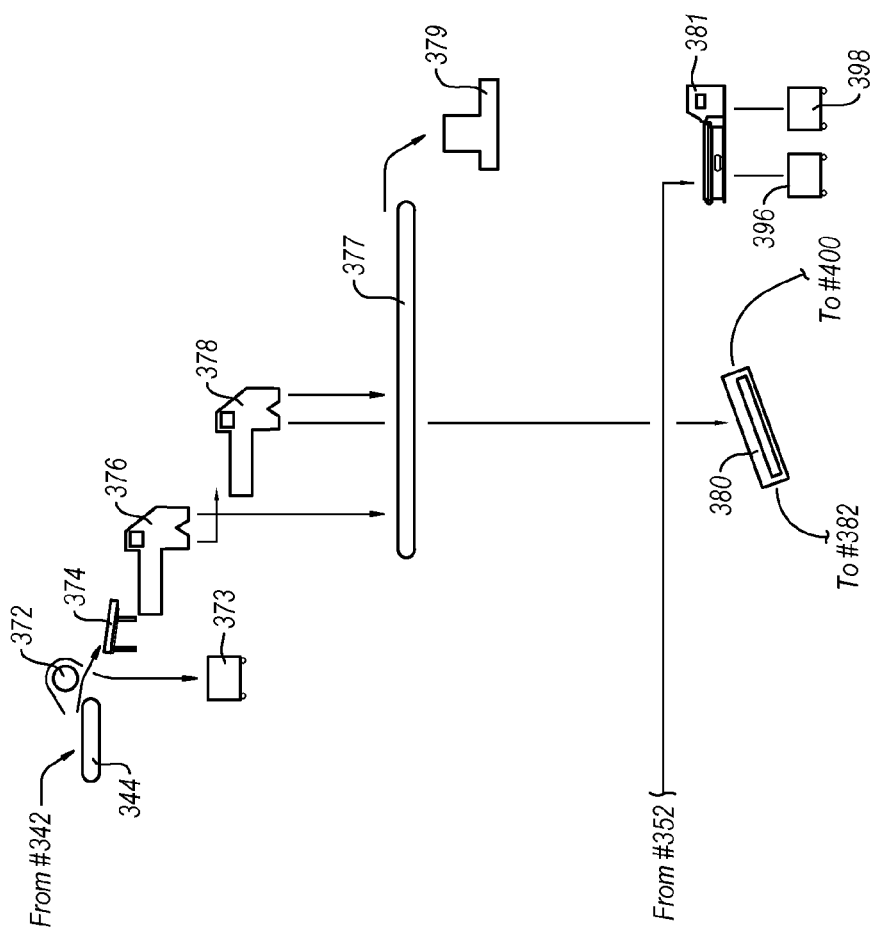
Figure 7:
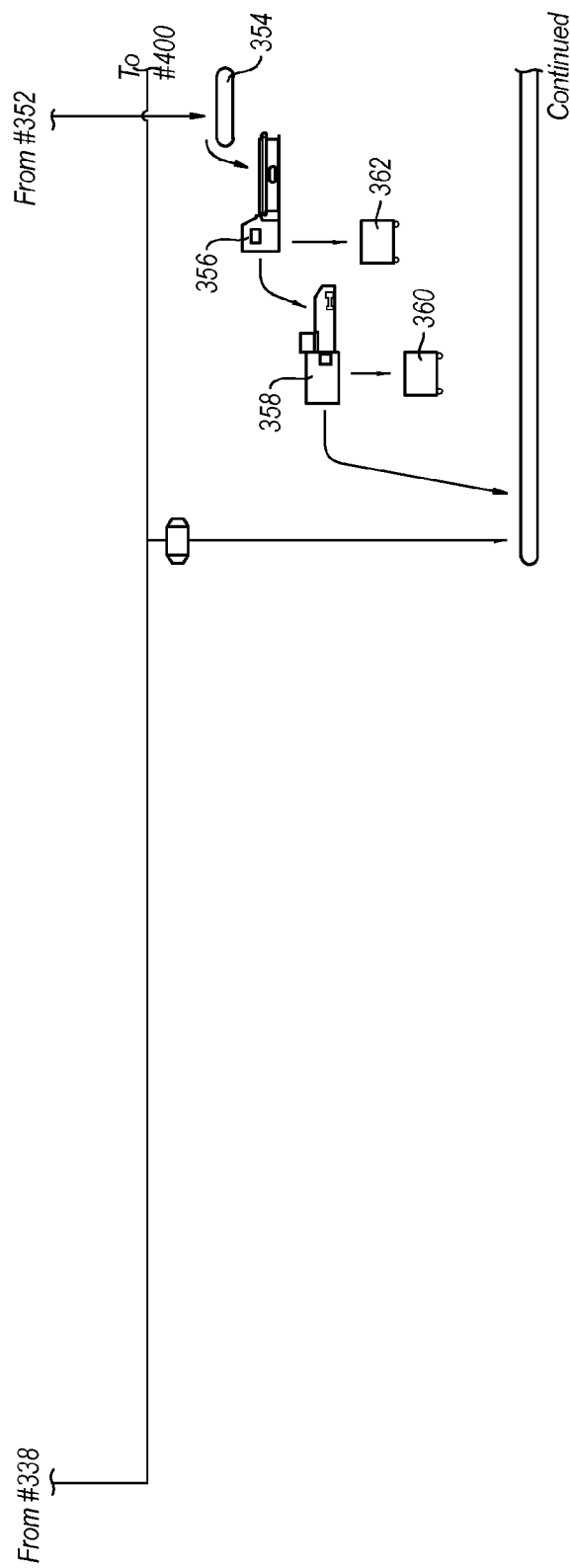
Figure 7:
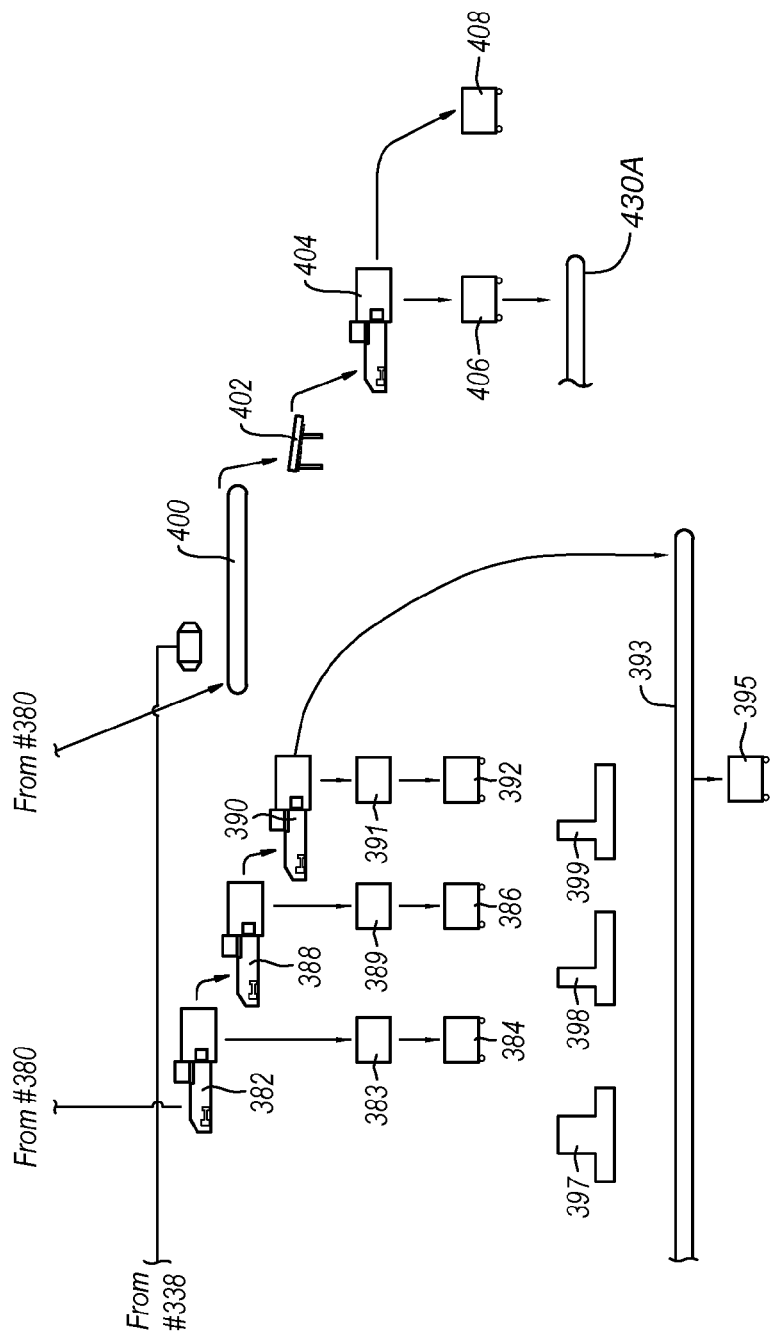
Figure 7:
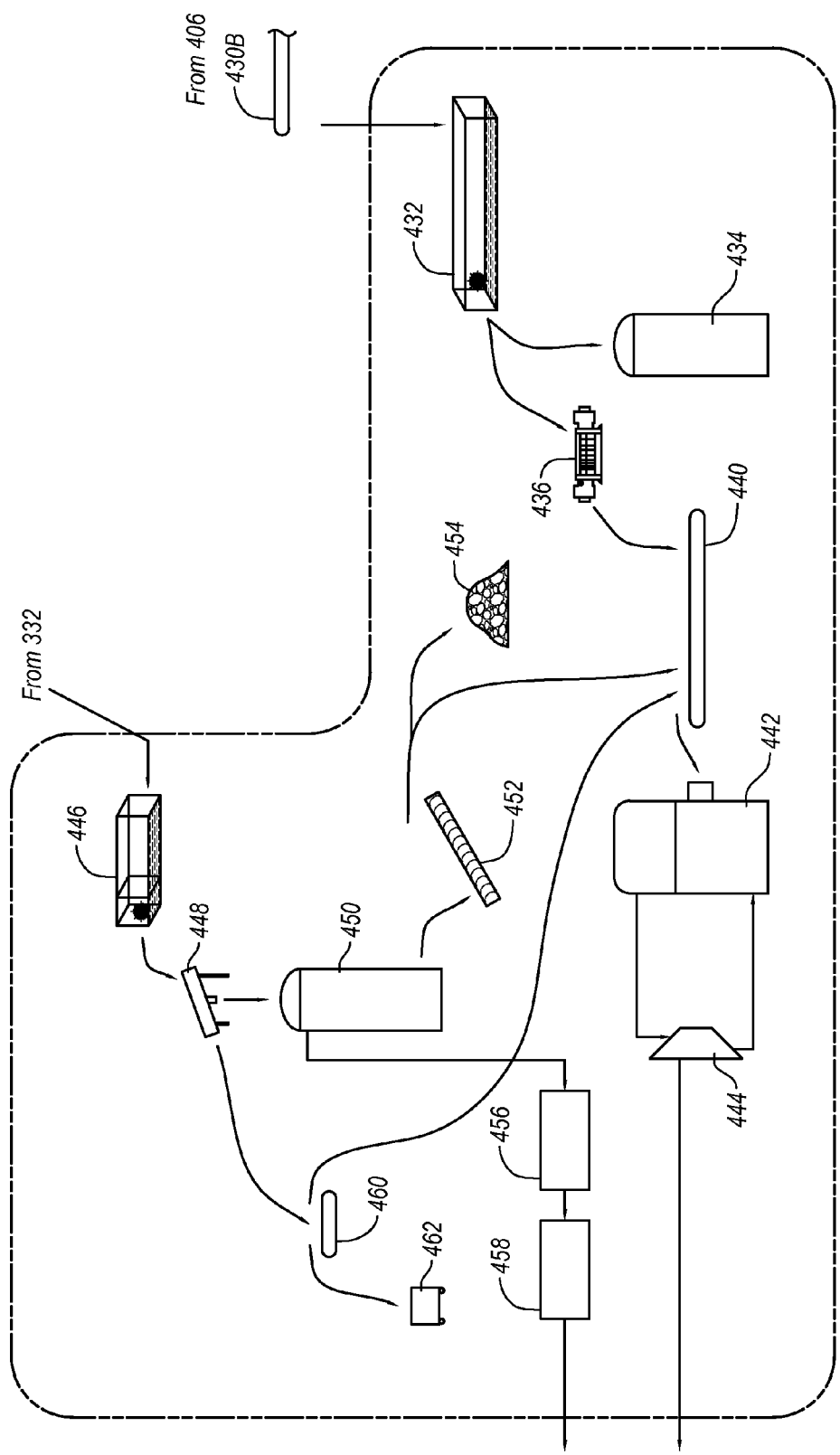

FIG. 7 illustrates a system 300 that can be used to separate wet and dry organic materials and recover renewable and recyclable products from a mixed waste stream. In FIG. 7, a mixed solid waste, such as municipal solid waste, is metered to a presorting conveyor 302. Metering may be carried out using a metering drum 304 and an infeed conveyor 306 that receives the mixed solid waste from a walking floor bunker feeder 308. Mixed solid waste on conveyor 302 is transferred to shredder or grinder 316. Mixed waste on conveyor 302 may be sorted manually. For example, manual laborers may pick large pieces of cardboard that are easily identifiable and selected out of large volumes of waste. Other materials may also be manually picked prior to shredding, grinding or size reduction, including large pieces of treated wood, electronic waste (e.g. eWaste) or other obviously valuable items that can be efficiently hand-picked or otherwise conveniently pulled from conveyor 302. Household Hazardous Waste (HHW) can also be removed from conveyor 302 and properly packaged and removed to the proper facility. Picked cardboard may be collected and stored in bin 310 or baled and shipped to a paper mill. Other recyclable materials such as non-ferrous and ferrous metals and/or other sources of recyclable materials may be collected and stored in bin 312 or additional bins. In addition, hazardous waste may be collected and stored in bin 314 and subsequently disposed of in a proper manner. While presorting is not required, pre-sorting can be particularly useful to avoid contamination from hazardous wastes and potential damage to the shredder from heavy ferrous structural metal, concrete, large stones and other items.

Material from conveyor 302 that is not picked is delivered to shredder or grinder 316, which shreds or grinds the waste to a desired top cut as described above. The shredded material is moved on a conveyor 318 under a suspended magnet 320, which collects ferrous metal exposed in the waste stream and delivers it to ferrous metal storage 322. Due to burden depth, the magnet 320 is preferably a suspended drum magnet although other magnets may be used alone or in combination with a suspended drum magnet. Drum magnets are advantageous due to the burden depth prior to size sorting and their ability to capture ferrous metal in flight after being discharged from the conveyor 318 therefore minimizing most non-metallic cross contamination of the extracted ferrous metal. Other types of magnets (e.g. cross belt magnets) can also be mounted in a fashion suspended above the conveyor belt headshaft.

Comminuted waste passing under magnet 320 is delivered to screens 324, which separates the comminuted waste stream by size to produce a first over fraction and a first under fraction. Screens 324 may include one screen or a plurality of similar and/or different sized screens and types of screens to produce one or more under fractions and one or more over fractions. The over fraction may be enriched in dry organics and under fraction may be enriched in wet organics.

The under fraction (i.e., fines) from screens 324 is conveyed on conveyor 326 to a second screen 328. The under fraction (i.e., fines) from second screen 328 may include wet organics and/or heavy inorganic materials, which may be processed using an eddy current separator 330 to recover non-ferrous metals. Conveyor 329 may be switchable to direct the fines from screen 328 to conveyor 336 if the inorganic fraction is dominant or to eddy current separator 330 if the wet organic is dominant. The wet organics from eddy current separator 330 can be collected and stored in bin 332 and the non-ferrous metals collected in bin 333.

The over fraction (i.e., coarse) from fine screen 328 may be further processed in density separator 334 to produce a light fraction having a small particle size and a heavy inorganic fraction. The heavy inorganic fraction can be conveyed to conveyor 336 and the light fraction can optionally be loaded in a second density separator 338 for additional separation into a light dry organic fraction and a heavy wet organic fraction.

With reference now to the first over fraction (from screen 324), the over fraction is conveyed on conveyor 340 to third density separator 342. Third density separator 342 can be configured to produce a light intermediate stream and a heavy intermediate stream. For example, third density separator 342 may be configured to cut in a range from 8-15 lbs. The light intermediate stream (i.e., less than 8-15 lbs) may be enriched in dry plastics, paper, light ferrous metals (e.g. tin cans and tin can lids and other light ferrous metal items) and light non-ferrous metals (e.g., aluminum cans and other light non-ferrous items), which are transferred to conveyor 344.

The heavy intermediate waste stream from third density separator 342 (i.e., greater than 8-15 lbs) may be enriched in heavy inorganic and heavy wet organic materials and heavy dry organic materials (e.g. wood and textiles), which are delivered to fourth density separator 346 for additional separation. Fourth density separator 346 may cut in a range from 60-120 lbs to produce a light intermediate stream, which is delivered to fifth density separator 364. The fifth density separator 364 may cut 40-60 lbs wet organic materials from 10-15 lbs dry organic materials consisting of primarily of wood and textiles. Fourth density separator 346 may also produce a heavy intermediate stream (i.e., greater than 60-120 lbs) enriched in heavy inorganic waste, which is delivered to conveyor 336. The intermediate stream on conveyor 336 may be sorted using a suspended drum magnet to collect ferrous metal and the remainder of the stream loaded on a vibratory feeder 350 that feeds an eddy current separator 352, which separates non-ferrous metal from the residue of inorganic waste. The non-ferrous metals may be further separated in infrared or other sorter 381 to extract copper and/or brass from other non-ferrous metals (i.e., to produce a mixed non-ferrous product stored in bin 396 and a brass and/or copper product stored in bin 398). The non-ferrous metals may be baled and/or bulk stored for shipment to mills.

The remainder of the waste stream exiting eddy current separator 352 is loaded on conveyor 354 and further processed using stainless steel sorter 356 and glass optical sorter 358. The intermediate stream may be sorted to extract stainless steel using stainless steel sorter 356 and/or sorted to extract glass using optical sorter 358. The sorting can produce recyclable stainless steel product and recyclable glass products, which can be stored in bins 362 and 360, respectively.

With reference again to fifth density separator 364, the light intermediate stream from separator 346 can be fractionated at a density of up to 15 lbs for the wood and textiles to 40 lbs-60 lbs for the heavy wet organics to produce a light intermediate waste stream enriched in wood and textiles. The wood and textiles can be separated on 2D-3D sorter such as ballistic or angled disc screen separator or other type of 2D-3D separator 366 to yield-three dimensional recyclable or renewable wood product and a two-dimensional recyclable or renewable textile product, which can be collected in bins 368 and 320, respectively. The heavy stream from separator 364 may be enriched in heavy wet organics and can be delivered to eddy current separator 330 and/or joined with waste from screens 328 and density separator 338.

With reference again to conveyor 344, the intermediate light stream from density separator 342 may be processed by suspension magnet 372 to yield a recyclable ferrous metal product collected in bin 373. The portion of intermediate stream that passes under magnet 372 and onto vibratory feeder 374 is loaded into a series of eddy current separators 376 and 378, which process the intermediate stream to recover non-ferrous metals. The non-ferrous metals may be collected on conveyor 377 and compacted into bales using baler 379 and then stored for shipment.

The dry organics not recovered in eddy current separators 376 and 378 provide an intermediate stream enriched in paper and plastics. The intermediate stream enriched in paper and plastics can be processed using a 2D-3D separator such as ballistic or angled disc screen separator or other type of 2D-3D separator 380. Ballistic or angled disc screen separator or other type of 2D-3D separator 380 separates plastic films and/or paper (i.e., 2D particles) from three-dimensional particles such as fractured rigid plastics. The 2D-3D separator can be placed before or after the suspended magnet 372 and eddy current separators 376 and 378.

The two-dimensional materials from ballistic or angled disc screen separator or other type of 2D-3D separator 380 can be delivered to conveyor 400 and the three-dimensional material can be further processed using optical sorters. The three-dimensional material can be processed in a first optical sorter 382 to produce an HDPE plastic product or PETE plastic product or #3-7 plastic product that is deposited onto quality control conveyor 383 and deposited into bin 384 or baled in baler 385. The intermediate stream can then be processed in a second optical sorter 388 to produce a PETE plastic product or HDPE plastic product or #3-7 plastic product that is deposited onto quality control conveyor 389 and deposited into bin 386 or baled in baler 387. Finally, the intermediate waste stream may be processed in a third optical sorter 390 to produce a recyclable #1-7 plastics product or HDPE plastic product or PETE plastic product that is deposited onto quality control conveyor 391 and deposited into bin 392 or baled in baler 397. The remainder of the waste stream from optical sorters 382, 388 and 390 may be a non-recyclable or renewable residual material or an improperly sorted recyclable material (e.g., PVC, stones, foam, eWaste, plastic bottle full of liquid, fragment of an aluminum can, etc.), which may be recovered on conveyor 393 and/or deposited into bin 395 or sent to a transfer trailer prior to being disposed of in a landfill or further separated into potentially recyclable fractions of mixed inorganic material and transformed into various building materials that can potentially be marketed or used in construction applications.

With reference now to the two-dimensional material received on conveyor 400 from ballistic or angled disc screen separator or other type of 2D-3D separator 380, the two-dimensional material may be an intermediate stream enriched in film plastic and mixed paper. The two-dimensional materials may be loaded into a dosing bin or other type of metered storage and feeding device 402 and then metered to a plurality (e.g., 2-12) of optical sorters 404 that are configured to separate film plastics and rigid plastics from paper. Optical sorters 404 produce a recyclable highly concentrated plastic film product or fuel 406 and a recyclable or renewable mixed paper product 408, either or both of which may be baled and/or stored for sale or shipment.

Wet organics produced in system 300 (e.g., wet organics in bin 332) and any or all of the dry organics can be further processed using the conversion techniques described above. In one embodiment a plastic film product 406 or mixed plastic can be transferred to conveyor 430A and delivered to material storage bunker 432. From material storage bunker the plastic product can be processed into a renewable fuel in a plastics conversion process 434. Alternatively the plastic product can be shredded in shredder 436 and conveyed on conveyor 440 to a gasifier 442. Gasifier 442 can produce heat to drive turbine 444 and produce electricity or produce mechanical power. In an alternative embodiment, mixed paper or mixed paper 408 or mixed paper and plastic can be transferred to conveyor 430 and delivered to gasifier 442.

Wet organics produced in system 300 (e.g., wet organics in bin 332) can be further processed, composted, provided to or sold to a processor as a highly concentrated mixed wet organics stream (e.g. food waste and yard waste and green waste). FIG. 7 illustrates embodiments for converting wet organics to higher value products such as biogas or electricity. Wet organics from bin 332 are transferred to a metering/storage bin 446 to be fed to a preprocessing apparatus 448. Preprocessing apparatus 448 may be a separator such as a Scott turbo separator that has breaker bars that crush particles to be fed into anaerobic digester 450 and eject flexible items like rubber and textiles, which can be ejected to conveyor 460 and either sent to residue bin 462 or delivered to conveyor 440 to be gasified, if appropriate.

Anaerobic digester 450 produces biogas and a digestate. The digestate may be dewatered using dewatering apparatus 452. Separated digestate can be stored in bulk storage 454 or delivered to conveyor 440 for gasification in gasifier 442. Solids from the digestate may be dried and/or composted to produce a soil amendment.

Biogas produced in digester 450 can be conditioned before being combusted in an internal combustion engine 458 to produce electricity. Biogas conditioner 458 may include an absorbent that absorbs pollutants and/or carbon dioxide. Electricity produced from combustion engine 458 may be used on-site to power components of the waste processing system and/or may be placed on an electrical grid for use by the consuming public. The biogas conditioner can be regenerated periodically to maintain its ability to absorb pollutants.

The dry organic fuel products can, for example, be used alone or with another fuel in place of coal and other carbon based fuels in a number of industrial and energy generation processes. The dry organic fuel can also be used as a fuel to make synthesis gas through a variety of high temperature thermal conversion processes (e.g. gasification, plasma arc gasification and pyrolysis.) The dry organic material may also be stored on-site in either a bulk storage building with an automated filling and discharge system or storage silos with unloading devices.

Those skilled in the art will recognize that the recyclable products produced using the methods described herein are highly enriched in a particular type of recyclable material, which makes the one or more different products useful as a feed material in a recycling process. Nevertheless, the recyclable products are usually not 100% pure. While the recycling industry cannot use raw unprocessed refuse, most recycling systems can properly operate with small amounts of impurities. The systems and methods of the invention are used to produce recycled products having a suitable purity for use in the recycling industry.

It is also desired to transform the recovered recyclables into new products using conventional manufacturing techniques (e.g. paper pulping to papermaking, production of aluminum ingot from aluminum cans, PETE bottle to PETE bottle manufacturing, PETE to insulation, HDPE to HDPE bottles or packaging materials, glass to construction materials, etc.) versus selling the recycled materials into conventional recycling materials markets.

While it may be desirable to recover value from essentially all the components of a solid waste stream, the present invention includes embodiments in which all or a portion of the wet organic fraction, dry organic fraction, or inorganic fraction is not fully separated into a recovered product. For example, in one embodiment all or a portion of the wet organic fraction, dry organic fraction, or inorganic fraction, whether mixed, properly separated, or improperly separated may simply be landfilled depending on the purity of the particular fraction and/or the market conditions for recycling the particular fraction (e.g., film may be landfilled).

While many of the methods and systems disclosed herein have been described as including density separation, those skilled in the art will recognize that in some embodiments, sufficient separation can be achieved without density separation, so long as the waste stream is comminuted and separated by size to produce intermediate streams enriched in at least one recoverable material.

Additional embodiments of the invention include systems and methods that incorporate one or more features of the systems and methods described in U.S. Provisional Patent Application Nos. 61/298,208, filed Jan. 25, 2010; 61/308,243, filed Feb. 25, 2010; and 61/417,216, filed Nov. 24, 2010; and/or U.S. Non-provisional patent application Ser. No. 12/897,996; all of which are hereby incorporated by reference in their entirety.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

We claim:

1. A method for processing mixed solid waste, comprising:
providing a mixed waste stream including household and/or commercial solid waste, the mixed waste comprising at least 10 wt % wet organic waste and at least 10 wt % dry organic waste that is comingled;
comminuting and sizing the mixed waste to produce a sized waste stream with a lower cutoff size greater than 2 inches and an upper cutoff less than 18 inch;
separating the wet organic waste from the dry organic waste in the sized waste stream using at least one mechanical separator to produce an intermediate wet organic stream and an intermediate dry organic stream, wherein the separation has a throughput of at least 10 metric tons per hour of mixed waste;
converting at least a portion of the intermediate wet organic stream to one or more of a renewable fuel products, a soil amendment, a liquid fertilizer, a compost, energy, or a combination thereof using at least a first conversion technique; and
converting the intermediate dry organic stream to one or more of a renewable fuel products, a chemical compound product, energy or a combination thereof using at least a second conversion technique, wherein the second conversion technique is different than the first conversion technique.

2. A method as in claim 1, wherein less than 40 wt % of the mixed waste stream is separated as a recovered product using manual labor.

3. A method as in claim 1, wherein less than 1 wt % of the mixed waste stream is separated as a recovered product using manual labor.

4. A method as in claim 1, wherein the mixed waste stream includes at least 15% dry organic waste and at least 30% wet organic waste.

5. A method as in claim 1, wherein at least 10 wt % of the mixed waste stream is dry organic waste selected from the group consisting of 3-dimensional plastic, film plastic, paper, cardboard, rubber, textiles, and wood.

6. A method as in claim 1 wherein at least 10 wt % of the mixed waste stream is a wet organic waste selected from the group consisting of food waste, animal waste, yard waste and green waste.

7. A method as in claim 1, wherein the mechanical sorter includes a size separator, a density separator or a combination thereof.

8. A method as in claim 1, wherein the first conversion technique is selected from wet digestion, dry digestion, anaerobic digestion, aerobic digestion or composting.

9. A method as in claim 8, wherein the first conversion technique produces biogas.

10. A method as in claim 9, wherein the biogas is converted to a liquid fuel or electricity.

11. A method as in claim 1, wherein the first conversion technique includes digesting the organic waste in an induced blanket up-flow anaerobic digester.

12. A method as in claim 1, wherein the dry organic material is further dried using aerobic composting, air drying, solar drying, waste heat from burning biogas and/or from burning dry organic material prior to being converted by the second conversion technique.

13. A method as in claim 1, wherein the separation of the wet organic from the dry organic materials yields a dry organic material having less than 25% moisture content and the dry organic material is converted to a refuse derived fuel.

14. A method as in claim 1, wherein the second conversion technique includes compacting dry organic material and/or thermally oxidizing the dry organic material to produce electrical power and/or heat.

15. A method as in claim 1, wherein the mixed waste stream included at least 20% by weight of low value material selected from the group consisting of wet organics, green waste, food waste, grit, fines less than 1 inch, asphalt, concrete, textiles, wood, rubber, film plastic, PVC, foil, rock, used consumer products, low value glass, composite materials, and combinations of these.

16. A method as in claim 1, wherein the dry organic waste is enriched in plastics, the second conversion technique comprising sorting the dry organic material by separating 3-dimensional plastics from 2-dimensional plastics to yield a 3-dimensional recyclable plastic product.

17. A method as in claim 16, wherein the 2-dimensional plastic is converted to a fuel and the 3-dimensional plastic is recycled to form a plastic product.

18. A method as in claim 1, wherein the mixed waste stream includes inorganic waste, the method further comprising separating at least a portion of the inorganic waste from the wet organic waste material and the dry organic waste material to form an inorganic waste stream enriched in inorganic waste materials.

19. A method as in claim 1, wherein the mixed waste stream includes inorganic waste, the method further comprising:
separating at least a portion of the inorganic waste from the wet organic waste material and the dry organic waste material to increase purity of the wet organic and dry organic waste streams; and
recovering at least a portion of the dry organic material as a recyclable product.

* * * * *